United States Patent
Baba et al.

(10) Patent No.: US 6,817,245 B2
(45) Date of Patent: Nov. 16, 2004

(54) ACCELERATION SENSOR

(75) Inventors: Hiroyuki Baba, Kawasaki (JP); Noriyuki Murata, Sagamihara (JP)

(73) Assignee: Matsushita Electric Industrial Co., Ltd., Osaka (JP)

(*) Notice: Subject to any disclaimer, the term of this patent is extended or adjusted under 35 U.S.C. 154(b) by 0 days.

(21) Appl. No.: 10/839,996

(22) Filed: May 6, 2004

(65) Prior Publication Data

US 2004/0206177 A1 Oct. 21, 2004

Related U.S. Application Data

(62) Division of application No. 09/870,030, filed on May 30, 2001, now Pat. No. 6,769,305.

(30) Foreign Application Priority Data

May 30, 2000 (JP) ........................ 2000-159445
Jun. 21, 2000 (JP) ........................ 2000-186524

(51) Int. Cl.⁷ ............................................. G01L 11/08
(52) U.S. Cl. ..................... 73/514.34; 73/654; 73/35.11; 310/329
(58) Field of Search ............................. 73/514.34, 654, 73/35.11, 493; 310/329

(56) References Cited

U.S. PATENT DOCUMENTS

| | | | |
|---|---|---|---|
| 4,660,410 A | 4/1987 | Asano et al. | 310/329 |
| 5,635,629 A | 6/1997 | Imai et al. | 73/35.11 |

FOREIGN PATENT DOCUMENTS

| | | |
|---|---|---|
| EP | 0 721 108 A | 10/1996 |
| JP | 62-103526 | 5/1987 |
| JP | 7-218370 | 8/1995 |
| JP | 8-304169 | 11/1996 |
| JP | 10-48041 | 2/1998 |

*Primary Examiner*—John E. Chapman
(74) *Attorney, Agent, or Firm*—Pearne & Gordon LLP

(57) ABSTRACT

An acceleration sensor for detecting an acceleration caused by an object oscillated in an oscillation direction, comprises a sensor casing having a center axis that is positioned in coaxial alignment with the oscillation direction to receive the acceleration, an oscillation plate and a piezoelectric element. The sensor casing has first and second circular inner surfaces opposing to and spaced apart along the center axis from each other at a first space distance, and a third cylindrical inner surface connected at one end with the first inner surface and at the other end with the second inner surface to define a cylindrical closed space. The oscillation plate is accommodated in the closed space of the sensor casing and has a central portion securely supported by the sensor casing and a peripheral portion integrally formed with the central portion and extending radially outwardly of the central portion. The piezoelectric element is provided on the oscillation plate to generate a voltage indicative of the acceleration. The sensor casing is provided with a cover member. The resonance frequency of the sensor casing is greater than or equal to the resonance frequency of the oscillation plate multiplied by 3, the modulus of elasticity in bending of the cover member is greater than or equal to $8 \times 10^3$ (MPa), and the logarithmic decrement of the cover member is greater than or equal to 8 (1/s).

21 Claims, 31 Drawing Sheets

F I G. 3
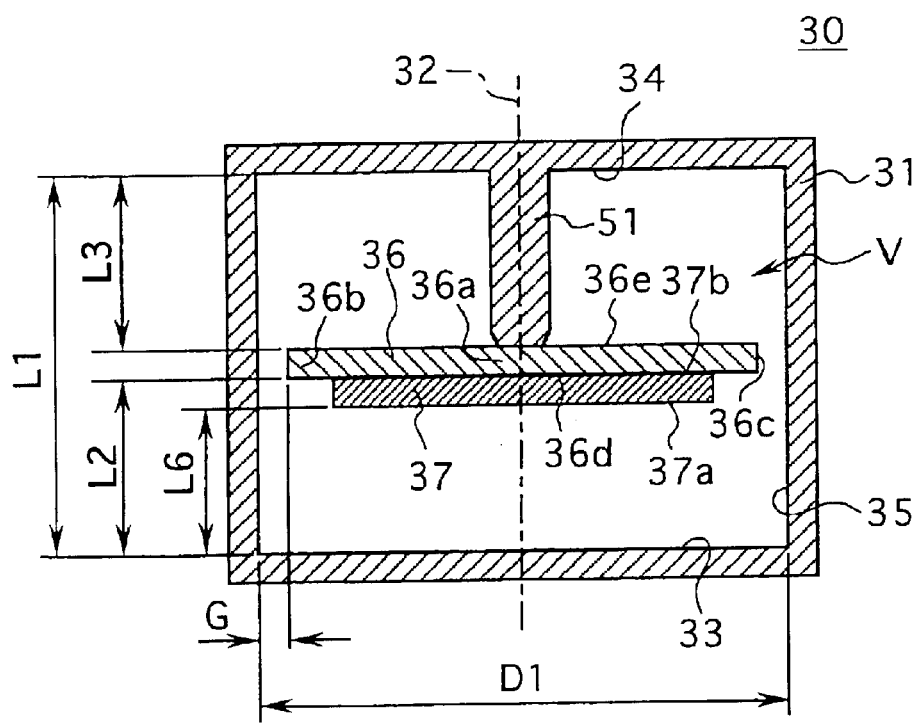

F I G. 1 0
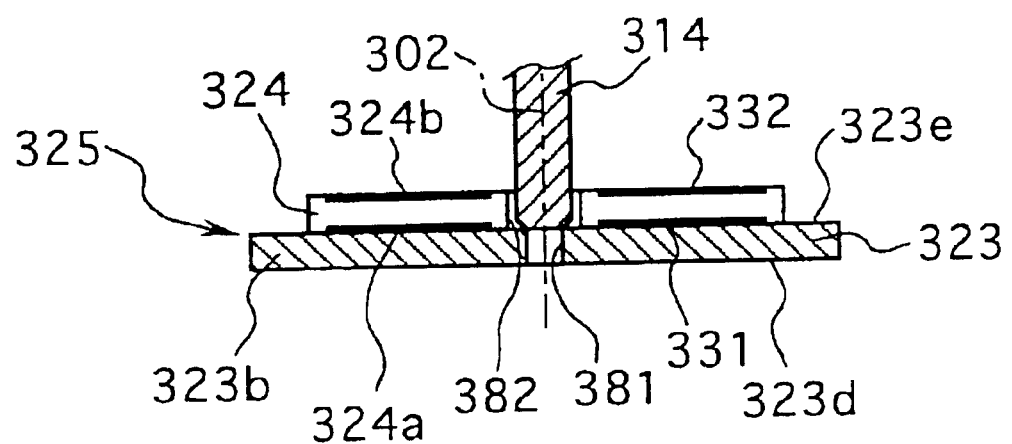

FIG. 22

| D2＼D1 | φ18.4 | φ16.9 |
|---|---|---|
| φ24 | 1.30 | 1.42 |
|  | ○ | × |
| φ21.5 | 1.17 | 1.27 |
|  | ○ | ○ |

ACCELERATION SENSOR

BACKGROUND OF THE INVENTION

1. Field of the Invention

The present invention relates to an acceleration sensor, and more particularly to an acceleration sensor for detecting an acceleration caused by an object with a piezoelectric element mounted on an oscillation plate accommodated in a sensor casing.

2. Description of the Related Art

In general, the acceleration sensor now known and in use includes various types such as an electromagnetic type, a piezoelectric element type, and a semiconductor type, all of which are designed to detect the acceleration. Among these types of acceleration sensors, the piezoelectric element type of acceleration sensor is known as detecting acceleration with a piezoelectric element when it is deformed to generate a voltage indicative of the acceleration. These types of acceleration sensors are usually mounted on automobiles to be used for controlling knockings of engines and airbag systems.

The acceleration sensor of this type is raised for example as a first conventional acceleration sensor and shown in FIGS. 25 and 26. The acceleration sensor 800 comprises a fixed case member 801, an oscillation plate 802, a piezoelectric element 803, electrodes 804, a metal wire 805, a cover member 806, an output terminal pin 807 and a resilient ring 808. The fixed case member 801 formed in a cylindrical shape is made of a metal and has a supporting portion 801a upwardly projecting from and integrally formed with the bottom portion of the fixed case member 801. The oscillation plate 802 formed in an annular shape is made of a metal and securely mounted on the supporting portion 801a of the fixed case member 801 by welding. The piezoelectric element 803 formed in an annular shape is provided on the oscillation plate 802 in axial alignment with the oscillation plate 802. The piezoelectric element 803 is covered with the electrodes 804. One of the electrodes 804 is electrically connected with the oscillation plate 802, while the other of the electrodes 804 is electrically connected with the output terminal pin 807. The electrical connection between the other of the electrodes 804 and the output terminal pin 807 is established by the metal wire 805 having both ends soldered at 805a by wire bonding and like. The cover member 806 formed in a cylindrical shape is made of a plastic material and has an exterior object mounted thereon and electrically connected with the output terminal pin 807. The output terminal pin 807 is mounted on the cover member 806. The fixed case member 801 and the cover member 806 have respectively peripheral edge portions 801c and 806c bent and fixedly coupled with each other with the resilient ring 808 intervening between the peripheral edge portions 801c and 806c to hermetically seal the gap and define a closed space in which the oscillation plate 802 and the piezoelectric element 803 are operatively accommodated. Therefore, no water enters the closed space through the gap.

Another acceleration sensor of the piezoelectric element type is raised for example as a second conventional acceleration sensor and shown in FIG. 27.

The acceleration sensor 900 comprises a fixed case member 901, a metal base member 902, an oscillation plate 802, a piezoelectric element 803, electrodes 804, a metal plate 903, a cover member 904, an output terminal pin 807 and a resilient ring 905. The fixed case member 901 formed in a cylindrical shape has an annular ledge portion 901c radially inwardly bent. The metal base member 902 formed in a circular shape and provided on the fixed case member 901 at the annular ledge portion 901c of the fixed case member 901. The cover member 904 formed in a circular shape has a peripheral edge portion 904a fixedly connected with the annular ledge portion 901c of the fixed case member 901 with the metal base member 902 intervening between the fixed case member 901 and the cover member 904. The fixed case member 901, the metal base member 902 and the cover member 904 collectively define a closed space to accommodate the oscillation plate 802 and the piezoelectric element 803 to be oscillatable by an oscillation exerted on the acceleration sensor. On the cover member 904 formed in a circular shape is Mounted the output terminal pin 807 electrically connected with the piezoelectric element 803 and connectable with an exterior connecting member. The metal base member 902 has a supporting portion 902a projecting toward the fixed case member 901 into the closed space and has the oscillation plate 802 and the piezoelectric element 803 securely supported thereon. In this example, both of the oscillation plate 802 and the piezoelectric element 803 are formed in an annular shape, and the cover member 904 is made of a plastic material to ensure that the output terminal pin 807 is electrically insulated from the metal base member 902. Through the supporting portion 902a of the metal base member 902 is extending the output terminal pin 807 which has one end electrically connected with one of the electrodes 804 of the piezoelectric element 803 through the metal plate 903 soldered by 903a and thus electrically connected with one of the electrodes 804 of the piezoelectric element 803 so that the oscillation plate 802 and the piezoelectric element 803 can be oscillated when they are exerted by an acceleration. The resilient ring 905 is interposed between the inner surface of the fixed case member 901 and the outer surface of the metal base member 902 to ensure that the resilient ring 905 hermetically seals the closed space. The rigidity of the metal plate 903 is preferably as small as possible and may be replaced by the metal wire 805 electrically connected with the electrode 804 of the piezoelectric element 803 and the output terminal pin 807, while the oscillation plate 802 may be connected to the supporting portion 902a by welding.

The above two type of acceleration sensors 800 and 900 have male screws 801b and 901b, respectively formed on its exterior side of the fixed case member 801 and 901 to be screwed into a female screw portion formed in a detectable object such as engine. Thus, the oscillation plate 802 is oscillated and deformed by an oscillation from the detectable object such as engine to have the piezoelectric element 803 generate a voltage. indicative of the acceleration, thereby enabling the voltage to be outputted from the electrodes 804 through the output terminal pin 807 with the fixed case member 801, 901 and the metal base member 902 earthed to the ground.

FIG. 28 is a graph showing a characteristic of the resonance frequency fo with respect to the oscillation under a predetermined acceleration of the acceleration sensor of these types, for example, obtaining a relatively high sharpness of resonance Q in the vicinity of a point of the resonance frequency fo while obtaining a relatively low and flat sharpness of resonance Q at intermediate and lower frequency range. Here, the sharpness of resonance Q means sensitivity of resonance. Generally available is the relatively high sharpness of resonance Q at around the point of the resonance frequency fo and the relatively low and flat sharpness of resonance Q at intermediate and lower frequency range any one of which is selected depending upon the acceleration sensor in use. Accordingly, the upper limit of the frequency range in substantial use is the point of the resonance frequency fo. For example, the sharpness of resonance Q in the vicinity of the point of the resonance frequency fo used for obtaining the desirable frequency makes it impossible to detect a frequency slightly out of the point of the resonance frequency fo. Generally, the disadvantages inherent in the foregoing apparatus is overcome with the resistance R and the piezoelectric element 803 connected in parallel relationship with each other to have the output voltage kept at relatively low level as shown in FIG. 29, thereby reducing the sharpness of the resonance Q to an appropriate value as indicated in a broken line in FIG. 28. In aspect of the sensitivity, the acceleration sensor 900 shown in FIG. 27 is found to be of a higher sensitivity than that of the acceleration sensor 800 shown in FIG. 25 through repeated experiments. This reason is considered to be due to the fact that the oscillation plate 802 is supported by the metal base member 902 so that the metal base member 902 without a perfect rigidity is oscillated together with the oscillation plate 802 by the acceleration exerted on the oscillation plate 802 and the metal base member 902, thereby making it possible the oscillation plate 802 to serve as an amplifying transformer. This type of the acceleration sensor is disclosed in the Japanese Patent Laid-Open Publication No. S58-142227.

The electrodes of the piezoelectric element 803 may include two different types such as a stimulus electrode with small diameter and a stimulus electrode with large diameter, which are positioned in coaxial alignment with an oscillation direction to receive the acceleration. An alternating current voltage from an exterior object is transmitted through the stimulus electrodes to deform the piezoelectric element 803, which enables the oscillation plate 802 to be oscillated. The oscillation of the oscillation plate 802 produces an electric potential from the electrodes 804 so that the function and failure of the acceleration sensor, and levels of the detection can be checked.

The previously mentioned conventional acceleration sensors 800 and 900 are of the type that the oscillation plate 802 is supported by the supporting portions 801a or 902a. Besides this type of the acceleration sensor, there are various types of acceleration sensor, for example, the type the oscillation plate is in the form of a circular shape and has a peripheral edge portion clamped and the type the oscillation plate is in the form of a rod shape and has one end fixed and the other end freely oscillatable in a cantilever fashion. Further, the above conventional acceleration sensors comprise, for example, the type between the electrodes 804 of the piezoelectric element 803 and the output terminal pin 807 is provided a print base plate accommodating therein an electric impedance transformer, an amplifier, a correction circuit and other electronic parts all of which are electrically connected with the metal wire 805. The above conventional acceleration sensors still further comprise the type having a single output terminal pin 807 provided in association with the fixed case member 801 and 901 to serve as an earth member. The other type of acceleration sensor having double terminal pins is known.

However, the acceleration sensors of the prior art possess their own distinct limitations. Generally, as shown in FIG. 30, the oscillation plate 802 and the piezoelectric element 803 of those acceleration sensors have resonance characteristics in the vicinity of the point of the resonance frequency fo. However, in the case of those conventional acceleration sensors, an acoustic standing wave can be generated in a certain size of the closed space in which the oscillation plate 802 and the piezoelectric element 803 are oscillatably accommodated. As shown in FIG. 31, in the event of generating two peaks of resonance in the vicinity of the point of the resonance frequency fo, a large anti-resonance peak (hereinafter "dip") can be generated because of their phase difference. This large dip can be the cause of spurious noise which deteriorates the characteristic of an acceleration sensor. In addition, in this case of those conventional acceleration sensors, an acoustic resonance can be generated in the closed space, which can be the cause of generating a dip. This dip can be also the cause of spurious noise which deteriorates the characteristic of an acceleration sensor.

As this spurious noise is generated by sound, the frequency of generating spurious noise varies according to the sonic speed u. For example, the sonic speed increases 1.18 times when the temperatures change from 20 to 120, which can be derived from the following equation.

$$u=331.45+0.607\, T(m/s)$$

wherein T indicates temperature.

From this equation, it is understood that a large dip that cannot be generated in room temperatures can sometimes be generated in high temperatures. On the contrary, a large dip that was small in high temperatures can also sometimes be generated in room temperatures. As the reason of generating spurious noise has not been solved, the conventional acceleration sensor has to be designed to have the desirable resonance frequency fo. In addition, the constructing of a conventional acceleration sensor is a complicated process, that is, the acceleration sensor has to be customized to have a structure to avoid spurious noise, which needs repeated change of the dimensions of the acceleration sensor components.

The acceleration sensor has the resonance frequency fo in the usable frequency range or broad frequency range. The complicated process described above causes another problem, that is, it is extremely difficult to design the sensor casing of the acceleration sensor to have standardized dimensions.

SUMMARY OF THE INVENTION

It is therefore a primary object of the present invention to provide an acceleration sensor which is excellent in characteristic.

It is another object of the present invention to provide an acceleration sensor which is simple in construction and thus inexpensive in production cost.

It is further object of the present invention to provide an acceleration sensor which is most appropriate for automatic production of acceleration sensors.

In accordance with a first aspect of the present invention, there is provided an acceleration sensor for detecting an acceleration caused by an object oscillated in an oscillation direction, comprising a sensor casing, an oscillation plate and a piezoelectric element. The sensor casing has a center axis and is positioned in coaxial alignment with the oscillation direction to receive the acceleration, the sensor casing has a first and second circular inner surfaces opposing to and spaced apart along the center axis from each other at a first space distance, and a third cylindrical inner surface connected at one end with the first inner surface and at the other end with the second inner surface to define a cylindrical closed space. The oscillation plate is accommodated in the closed space of the sensor casing and has a central portion securely supported by the sensor casing and a peripheral portion integrally formed with the central portion and extending radially outwardly of the central portion to be freely movable with respect to the sensor casing. The oscillation plate has a peripheral end surface spaced apart from the third inner surface of the sensor casing at an annular gap small enough to enable the oscillation plate to oscillate with respect to the sensor casing. The oscillation plate also has a first flat surface opposing to and spaced apart along the center axis from the first inner surface of the sensor casing at a second space distance, and a second flat surface opposing to and spaced apart along the center axis from the second inner surface of the sensor casing at a third space distance, with the oscillation plate being partly oscillatable along the center axis with respect to the sensor casing. The piezoelectric element has a first and second surface and is provided on at least one of the first and second flat surfaces of the oscillation plate to generate a voltage indicative of the acceleration. The first space distance is less than or equal to the diameter of the third inner surface of the sensor casing multiplied by 0.1.

In accordance with a second aspect of the present invention, there is provided an acceleration sensor for detecting an acceleration caused by an object oscillated in an oscillation direction, comprising a sensor casing, an oscillation plate, a first piezoelectric element and a second piezoelectric element. The sensor casing and oscillation plate are the same as in the first aspect of the invention. The first piezoelectric, element has first and second surfaces and is provided on the first flat surface of the oscillation plate to generate a voltage indicative of the acceleration, and the second piezoelectric element has first and second surfaces and is provided on the second flat surface of the oscillation plate to generate a voltage indicative of the acceleration. The first space distance is less than or equal to the diameter of the third inner surface of the sensor casing multiplied by 0.1.

In accordance with a third aspect of the present invention, there is provided an acceleration sensor for detecting an acceleration caused by an object oscillated in an oscillation direction, comprising a sensor casing, an oscillation plate, and a piezoelectric element. The sensor casing includes a cylindrical fixed case member having a circular bottom portion having a first circular inner surface, a cylindrical side portion integrally formed with the bottom portion, and a supporting portion projecting from the bottom portion, a cover member being provided on the fixed case member and having a circular cover portion having a second circular inner surface, and a cylindrical side portion integrally formed with the cover portion. The side portion of the fixed case member has a third cylindrical inner surface connected at one end with the first inner surface, and the side portion of the cover member has a fourth cylindrical inner surface connected at one end with the second inner surface, with the second inner surface of the cover portion of the cover member opposing to and spaced apart along the center axis from the first inner surface of the bottom portion of the fixed case member at a first space distance. The first inner surface of the bottom portion of the fixed case member, the third inner surface of the side portion of the fixed case member, the second inner surface of the cover portion of the cover member, and the fourth inner surface of the side portion of the cover member collectively define a cylindrical closed space. The oscillation plate is accommodated in the closed space of the sensor casing and has a central portion securely supported by the supporting portion of the fixed case member of the sensor casing, and a peripheral portion integrally formed with the central portion and extending radially outwardly of the central portion. The oscillation plate has a first flat surface opposing to and spaced apart along the center axis from the first inner surface of the bottom portion of the fixed case member at a second space distance, and a second flat surface opposing to and spaced apart along the center axis from the second inner surface of the cover portion of the cover member at a third space distance. The piezoelectric element has a first surface held in contact with the second flat surface of the oscillation plate, and a second surface opposing to and spaced apart along the center axis from the second inner surface of the cover portion of the cover member at a fourth space distance. The piezoelectric element is provided on the second flat surface of the oscillation plate in axial alignment with the oscillation plate to generate a voltage indicative of the acceleration. The first space distance is less than or equal to the diameter of the third inner surface of the side portion of the fixed case member multiplied by 0.1, and in which the first space distance is less than or equal to the diameter of the fourth inner surface of the side portion of the cover member multiplied by 0.1.

In accordance with a fourth aspect of the present invention, there is provided an acceleration sensor for detecting an acceleration caused by an object oscillated in an oscillation direction, comprising a sensor casing, an oscillation plate and a piezoelectric element. The sensor casing includes a cylindrical fixed case member, a metal base member, and a cover member. The cylindrical fixed case member has a circular bottom portion having a first circular inner surface, and a cylindrical side portion integrally formed with the bottom portion having a first section close to the bottom portion of the fixed case member, a second section remote from the bottom portion of the fixed case member and radially inwardly bent, and an annular ledge section formed between the first and second sections with an annular ledge. The metal base member has a circular base portion and a supporting portion with the base portion having a second circular inner surface and a circular outer surface, and the supporting portion projecting from the second inner surface. The base portion of the metal base member has a central section integrally formed with the supporting portion, and a peripheral section extending radially outwardly of the central section. The metal base member is mounted on the annular ledge of the fixed case member with a resilient ring intervening between the second section of the side portion of the fixed case member and the peripheral section of the base portion of the metal base member to hermetically seal the gap between the second section of the side portion of the fixed case member and the peripheral section of the base portion of the metal base member. The first section of the side portion of the fixed case member has a third cylindrical inner surface connected at one end with the first inner surface of the bottom portion of the fixed case member and at the other end with the second inner surface of the base portion of the metal base member, with the second inner surface of the base portion of the metal base member opposing to and spaced apart along the center axis from the first inner surface of the bottom portion of the fixed case member at a first space distance. The cover member is provided on the outer surface of the metal base member and has a peripheral section firmly engaged with the second section of the side portion of the fixed case member. The first inner surface of the bottom portion of the fixed case member, the second inner surface of the base portion of the metal base member, and the third inner surface of the first section of the side portion of the fixed case member collectively define a cylindrical closed space. The oscillation plate accommodated in the closed space of the sensor casing and having a central portion securely supported by the supporting portion of the metal base member of the sensor casing, and a peripheral portion integrally formed with the central portion and extending radially outwardly of the central portion. The oscillation plate has a first flat surface opposing to and spaced apart along the center axis from the first inner surface of the bottom portion of the fixed case member at a second space distance, and a second flat surface opposing to and spaced apart along the center axis from the second inner surface of the base portion of the metal base member at a third space distance. The piezoelectric element has a first surface opposing to and spaced apart along the center axis from the first inner surface of the bottom portion of the fixed case member at a fourth space distance, and a second surface held in contact with the first flat surface of the oscillation plate. The piezoelectric element being provided on the first flat surface of the oscillation plate in axial alignment with the oscillation plate to generate a voltage indicative of the acceleration. The first space distance is less than or equal to the diameter of the third inner surface of the first section of the side portion of the fixed case member multiplied by 0.1.

In accordance with a fifth aspect of the present invention, there is provided an acceleration sensor for detecting an acceleration caused by an object oscillated in an oscillation direction, comprising: a sensor casing having a center axis and to be positioned in coaxial alignment with the oscillation direction to receive the acceleration, the sensor casing including a cylindrical fixed case member having a circular bottom portion having a first circular inner surface, and a cylindrical side portion integrally formed with the bottom portion, the side portion of the fixed case member having a first section close to the bottom portion of the fixed case member, a second section remote from the bottom portion of the fixed case member and radially inwardly bent, and an annular ledge section formed between the first and second sections with an annular ledge, a metal base member having a circular base portion and a supporting portion, the base portion having a second circular inner surface and a circular outer surface, and the supporting portion projecting from the second inner surface, the base portion of the metal base member having a central section integrally formed with the supporting portion, and a peripheral section extending radially outwardly of the central section, the metal base member mounted on the annular ledge of the fixed case member with a resilient ring intervening between the second section of the side portion of the fixed case member and the peripheral section of the base portion of the metal base member to hermetically seal the gap between the second section of the side portion of the fixed case member and the peripheral section of the base portion of the metal base member, the first section of the side portion of the fixed case member having a third cylindrical inner surface connected at one end with the first inner surface of the bottom portion of the fixed case member and at the other end with the second inner surface of the base portion of the metal base member, the second inner surface of the base portion of the metal base member opposing to and spaced apart along the center axis from the first inner surface of the bottom portion of the fixed case member at a first space distance, and a cover member being provided on the outer surface of the metal base member and having a peripheral section firmly engaged with the second section of the side portion of the fixed case member, the first inner surface of the bottom portion of the fixed case member, the second inner surface of the base portion of the metal base member, and the third inner surface of the first section of the side portion of the fixed case member collectively defining a cylindrical closed space; an oscillation plate accommodated in the closed space of the sensor casing and having a central portion securely supported by the supporting portion of the metal base member of the sensor casing, and a peripheral portion integrally formed with the central portion and extending radially outwardly of the central portion to be freely movable with respect to the sensor casing, the oscillation plate having a peripheral end surface spaced apart from the third inner surface of the first section of the side portion of the fixed case member at an annular gap small enough to enable the oscillation plate to oscillate with respect to the sensor casing, the oscillation plate having a first flat surface opposing to and spaced apart along the center axis from the first inner surface of the bottom portion of the fixed case member at a second space distance, and a second flat surface opposing to and spaced apart along the center axis from the second inner surface of the base portion of the metal base member at a third space distance, the oscillation plate being partly oscillatable along the center axis with respect to the sensor casing; and a piezoelectric element having first and second surfaces and provided on at least one of the first and second flat surfaces of the oscillation plate in axial alignment with the oscillation plate to generate a voltage indicative of the acceleration when the acceleration is exerted on the sensor casing to have the oscillation plate partly oscillated along the center axis with respect to the sensor casing with the peripheral portion of the oscillation plate being deformed, the oscillation plate and the piezoelectric element collectively constituting an oscillation body; in which the resonance frequency of the sensor casing is more than or equal to the resonance frequency of the oscillation body multiplied by 3, and in which the modulus of elasticity in bending of the cover member is more than or equal to $8 \times 10^3$ (MPa), and the logarithmic decrement of the cover member is more than or equal to 8 (1/s).

In accordance with a sixth aspect of the present invention, there is provided an acceleration sensor for detecting an acceleration caused by an object oscillated in an oscillation direction, comprising: a sensor casing having a center axis and to be positioned in coaxial alignment with the oscillation direction to receive the acceleration, the sensor casing including a cylindrical fixed case member having a circular bottom portion having a first circular inner surface, and a cylindrical side portion integrally formed with the bottom portion, the side portion of the fixed case member having a first section close to the bottom portion of the fixed case member, a second section remote from the bottom portion of the fixed case member and radially inwardly bent, and an annular ledge section formed between the first and second sections with an annular ledge, a metal base member having a circular base portion and a supporting portion, the base portion having a second circular inner surface and a circular outer surface, and the supporting portion projecting from the second inner surface, the base portion of the metal base member having a central section integrally formed with the supporting portion, and a peripheral section extending radially outwardly of the central section, the metal base member mounted on the annular ledge of the fixed case member with a resilient ring intervening between the second section of the side portion of the fixed case member and the peripheral section of the base portion of the metal base member to hermetically seal the gap between the second section of the side portion of the fixed case member and the peripheral section of the base portion of the metal base member, the first section of the side portion of the fixed case member having a third cylindrical inner surface connected at one end with the first inner surface of the bottom portion of the fixed case member and at the other end with the second inner surface of the base portion of the metal base member, the second inner surface of the base portion of the metal base member opposing to and spaced apart along the center axis from the first inner surface of the bottom portion of the fixed case member at a first space distance, and a cover member being provided on the outer surface of the metal base member and having a peripheral section firmly engaged with the second section of the side portion of the fixed case member, the first inner surface of the bottom portion of the fixed case member, the second inner surface of the base portion of the metal base member, and the third inner surface of the first section of the side portion of the fixed case member collectively defining a cylindrical closed space; an oscillation plate accommodated in the closed space of the sensor casing and having a central portion securely supported by the supporting portion of the metal base member of the sensor casing, and a peripheral portion integrally formed with the central portion and extending radially outwardly of the central portion to be freely movable with respect to the sensor casing, the oscillation plate having a peripheral end surface spaced apart from the third inner surface of the first section of the side portion of the fixed case member at an annular gap small enough to enable the oscillation plate to oscillate with respect to the sensor casing, the oscillation plate having a first flat surface opposing to and spaced apart along the center axis from the first inner surface of the bottom portion of the fixed case member at a second space distance, and a second flat surface opposing to and spaced apart along the center axis from the second inner surface of the base portion of the metal base member at a third space distance, the oscillation plate being partly oscillatable along the center axis with respect to the sensor casing; a first piezoelectric element having first and second surfaces and provided on the first flat surface of the oscillation plate in axial alignment with the oscillation plate to generate a voltage indicative of the acceleration when the acceleration is exerted on the sensor casing to have the oscillation plate partly oscillated along the center axis with respect to the sensor casing with the peripheral portion of the oscillation plate being deformed; and a second piezoelectric element having first and second surfaces and provided on the second flat surface of the oscillation plate in axial alignment with the oscillation plate to generate a voltage indicative of the acceleration when the acceleration is exerted on the sensor casing to have the oscillation plate partly oscillated along the center axis with respect to the sensor casing with the peripheral portion of the oscillation plate being deformed, the oscillation plate and the first and second piezoelectric elements collectively constituting an oscillation body; in which the resonance frequency of the sensor casing is more than or equal to the resonance frequency of the oscillation body multiplied by 3, and in which the modulus of elasticity in bending of the cover member is more than or equal to $8 \times 10^3$ (MPa), and the logarithmic decrement of the cover member is more than or equal to 8 (1/s).

BRIEF DESCRIPTION OF THE DRAWINGS

The features and advantages of an acceleration sensor according to the present invention will more clearly be understood from the following description taken in conjunction with the accompanying drawings in which:

FIG. 3 is a cross-sectional view of the third embodiment of the acceleration sensor according to the present invention;

FIG. 10 is an enlarged and fragmentary cross-sectional view of the acceleration sensor shown in FIG. 9;

FIG. 22 is a table showing the experimental results obtained through the experiment of the acceleration sensor according to the present invention;

DESCRIPTION OF THE PREFERRED EMBODIMENTS

The first preferred embodiment of the acceleration sensor according to the present invention will now be described in detail in accordance with the accompanying drawings.

Figure 1:
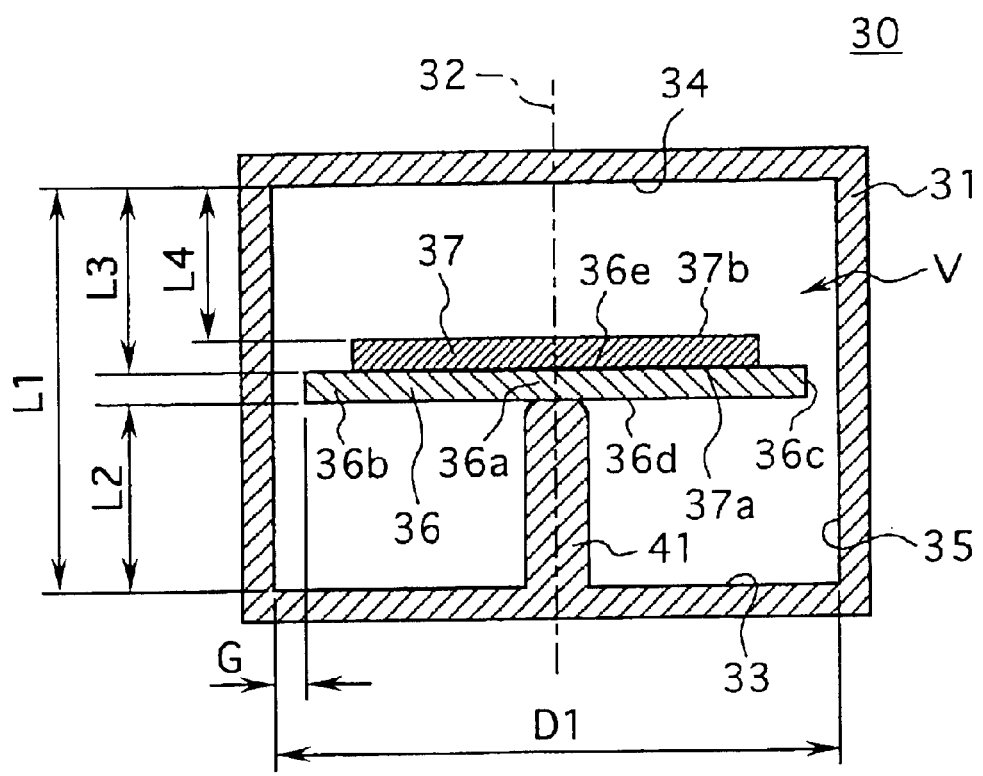
FIG. 1 is a cross-sectional view of the first embodiment of the acceleration sensor according to the present invention.

Referring now to the drawings, particularly to FIG. 1, the first preferred embodiment of the acceleration sensor is assumed to be installed on an engine of an automotive vehicle. The acceleration sensor 30 comprises a sensor casing 31 having a center axis 32 and to be positioned on the engine, not shown, in coaxial alignment with or otherwise in parallel relationship with an oscillation direction to receive an acceleration. More specifically, the oscillation direction is coincident with or otherwise in parallel relationship with the center axis 32 of the engine, i.e., the direction of the stroke of the engine to ensure detection of the acceleration acted on the engine. The above engine constitutes an object oscillated in the oscillation direction. The sensor casing 31 has first and second circular inner surfaces 33 and 34 opposing to and spaced apart along the center axis 32 of the sensor casing 31 from each other at a first space distance L1, and a third cylindrical inner surface 35 connected at one end with the first inner surface 33 and at the other end with the second inner surface 34 to define a cylindrical closed space V.

The acceleration sensor 30 further comprises an oscillation plate 36 accommodated in the closed space V of the sensor casing 31. The oscillation plate 36 has a central portion 36a securely supported by the sensor casing 31, and a peripheral portion 36b integrally formed with the central portion 36a and extending radially outwardly of the central portion 36a to be freely movable with respect to the sensor casing 31. The oscillation plate 36 has a peripheral end surface 36c spaced apart from the third inner surface 35 of the sensor casing 31 at an annular gap G small enough to enable the oscillation plate 36 to oscillate with respect to the sensor casing 31. The oscillation plate 36 has a first flat surface 36d opposing to and spaced apart along the center axis 32 of the sensor casing 31 from the first inner surface 33 of the sensor casing 31 at a second space distance L2, and a second flat surface 36e opposing to and spaced apart along the center axis 32 of the sensor casing 31 from the second inner surface 34 of the sensor casing 31 at a third space distance L3.

The fact that the oscillation plate 36 has a peripheral portion 36b extending radially outwardly of the central portion 36a to be freely movable with respect to the sensor casing 31 leads to the fact that the oscillation plate 36 can be partly oscillated along the center axis 32 of the sensor casing 31 with respect to the sensor casing 31. With the oscillation of the oscillation plate 36, the oscillation plate 36 can be deformed.

The acceleration sensor 30 further comprises a piezoelectric element 37 having first and second surfaces 37a and 37b and provided on at least one of the first and second flat surfaces 36d and 36e of the oscillation plate 36. The deformation of the peripheral portion 36b of the oscillation plate 36 causes the piezoelectric element 37 to generate a voltage indicative of the acceleration when the acceleration is exerted on the sensor casing 31 to have the oscillation plate 36 partly oscillated along the center axis 32 of the sensor casing 31 with respect to the sensor casing 31.

In the first embodiment of the acceleration sensor 30 according to the present invention, the first space distance L1 is less than or equal to the diameter D1 of the third inner surface 35 of the sensor casing 31 multiplied by 0.1.

The sensor casing 31 has a supporting portion 41 projecting from the first inner surface 33 toward the second inner surface 34 to support the oscillation plate 36. The piezoelectric element 37 is provided on the second flat surface 36e of the oscillation plate 36 to oppose and to be spaced apart along the center axis 32 of the sensor casing 31 from the second inner surface 34 of the sensor casing 31 at a fourth space distance L4.

In this embodiment, the second space distance L2 is less than or equal to the diameter D1 of the third inner surface 35 of the sensor casing 31 multiplied by 0.1, and the fourth space distance L4 is less than or equal to the diameter D1 of the third inner surface 35 of the sensor casing 31 multiplied by 0.1.

The piezoelectric element 37 provided on the second flat surface 36e of the oscillation plate 36 as shown in FIG. 1 may be replaced by a piezoelectric element provided on the first flat surface 36d of the oscillation plate 36 according to the present invention.

Figure 2:
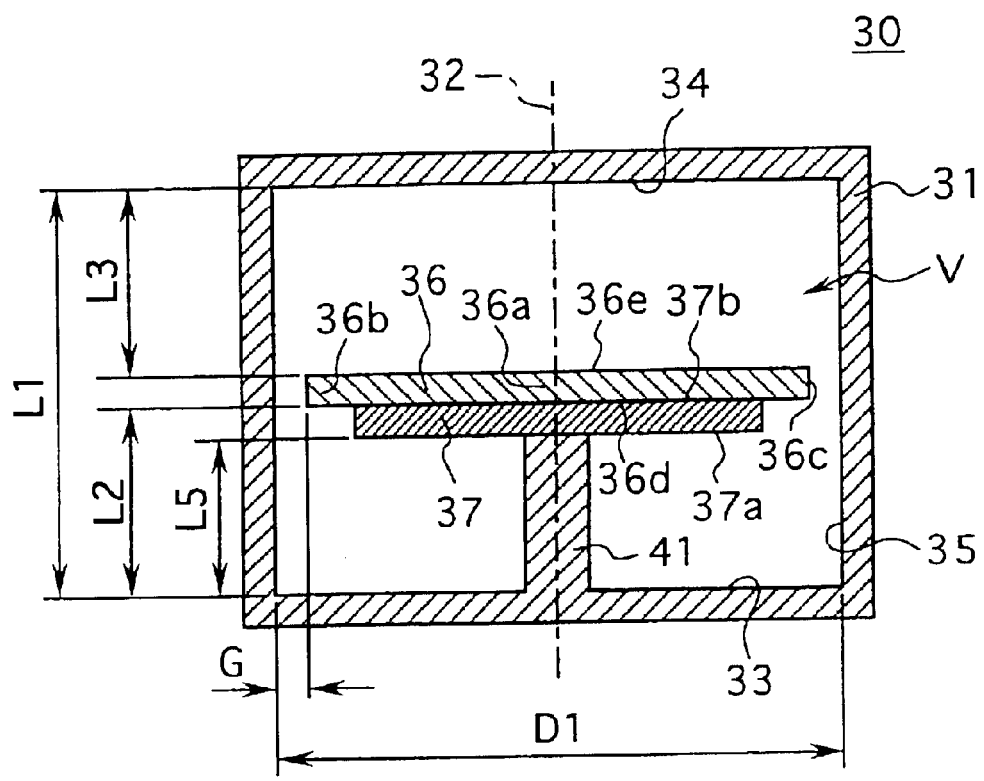
FIG. 2 is a cross-sectional view similar to FIG. 1 but showing the second embodiment of the acceleration sensor according to the present invention.

The second embodiment directed to the piezoelectric element provided on the first flat surface 36d of the oscillation plate 36 is shown in FIG. 2.

In FIG. 2, the sensor casing 31 has a supporting portion 41 projecting from the first inner surface 33 toward the second inner surface 34 to support the oscillation plate 36. The piezoelectric element 37 is provided on the first flat surface 36d of the oscillation plate 36 to oppose and to be spaced apart along the center axis 32 of the sensor casing 31 from the first inner surface 33 of the sensor casing 31 at a fifth space distance L5.

In this embodiment, the third space distance L3 is less than or equal to the diameter D1 of the third inner surface 35 of the sensor casing 31 multiplied by 0.1, and the fifth space distance L5 is less than or equal to the diameter D1 of the third inner surface 35 of the sensor casing 31 multiplied by 0.1.

The above description of the second embodiment has been made only about the oscillation plate 36 and the piezoelectric element 37 different from those of the first embodiment, but has not been directed to the sensor casing 31 and the supporting portion 41 which are entirely the same as those of the first embodiment. Detailed description about the sensor casing 31 and the supporting portion 41 will therefore be omitted hereinafter.

The third preferred embodiment of the acceleration sensor 30 according to the present invention will now be described in detail in accordance with the accompanying drawings.

Referring now to the drawings, particularly to FIG. 3, the third preferred embodiment of the acceleration sensor 30 is also assumed to be installed on an engine of an automotive vehicle in a similar fashion to the first and second embodiments. The acceleration sensor 30 comprises a sensor casing 31 having a center axis 32 and to be positioned in coaxial alignment with an oscillation direction to receive the acceleration. The sensor casing 31 has first and second circular inner surfaces 33 and 34 opposing to and spaced apart along the center axis 32 of the sensor casing 31 from each other at a first space distance L1 and a third cylindrical inner surface 35 connected at one end with the first inner surface 33 and at the other end with the second inner surface 34 to define a cylindrical closed space V.

The acceleration sensor 30 further comprises an oscillation plate 36 accommodated in the closed space V of the sensor casing 31. The oscillation plate 36 has a central portion 36a securely supported by the sensor casing 31, and a peripheral portion 36b integrally formed with the central portion 36a and extending radially outwardly of the central portion 36a to be freely movable with respect to the sensor casing 31. The oscillation plate 36 has a peripheral end surface 36c spaced apart from the third inner surface 35 of the sensor casing 31 at an annular gap G small enough to enable the oscillation plate 36 to oscillate with respect to the sensor casing 31. The oscillation plate 36 has a first flat surface 36d opposing to and spaced apart along the center axis 32 of the sensor casing 31 from the first inner surface 33 of the sensor casing 31 at a second space distance L2, and a second flat surface 36e opposing to and spaced apart along the center axis 32 of the sensor casing 31 from the second inner surface 34 of the sensor casing 31 at a third space distance L3.

The fact that the oscillation plate 36 has a peripheral portion 36b extending radially outwardly of the central portion 36a to be freely movable with respect to the sensor casing 31 leads to the fact that the oscillation plate 36 can be partly oscillated along the center axis 32 of the sensor casing 31 with respect to the sensor casing 31. With the oscillation of the oscillation plate 36, the oscillation plate 36 can be deformed. The acceleration sensor 30 further comprises a piezoelectric element 37 having first and second surfaces 37a and 37b and provided on at least one of the first and second flat surfaces 36d and 36e of the oscillation plate 36. The deformation of the peripheral portion 36b of the oscillation plate 36 causes the piezoelectric element 37 to generate a voltage indicative of the acceleration when the acceleration is exerted on the sensor casing 31 to have the oscillation plate 36 partly oscillated along the center axis 32 of the sensor casing 31 with respect to the sensor casing 31.

The sensor casing 31 has a supporting portion 51 projecting from the second inner surface 34 toward the first inner surface 33 to support the oscillation plate 36. The piezoelectric element 37 is provided on the first flat surface 36d of the oscillation plate 36 to oppose and to be spaced apart along the center axis 32 of the sensor casing 31 from the first inner surface 33 of the sensor casing 31 at a sixth space distance L6.

In this embodiment, the third space distance L3 is less than or equal to the diameter D1 of the third inner surface 35 of the sensor casing 31 multiplied by 0.1, and the sixth space distance L6 is less than or equal to the diameter D1 of the third inner surface 35 of the sensor casing 31 multiplied by 0.1.

The piezoelectric element 37 provided on the first flat surface 36d of the oscillation plate 36 as shown in FIG. 3 may be replaced by a piezoelectric element provided on the second flat surface 36e of the oscillation plate 36 according to the-present invention.

Figure 4:
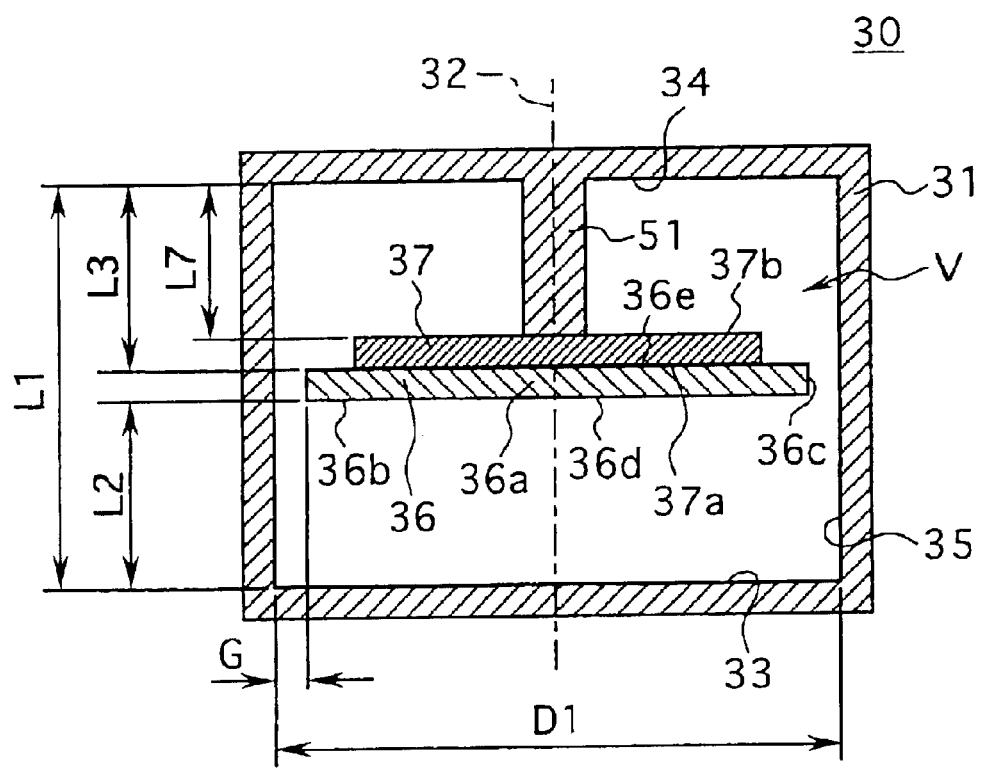
FIG. 4 is a cross-sectional view similar to FIG. 3 but showing the fourth embodiment of the acceleration sensor according to the present invention.

The fourth embodiment directed to the piezoelectric element provided on the second flat surface 36e of the oscillation plate 36 is shown in FIG. 4.

In FIG. 4, the sensor casing 31 has a supporting portion 51 projecting from the second inner surface 34 toward the first inner surface 33 to support the oscillation plate 36. The piezoelectric element 37 is provided on the second flat surface 36e of the oscillation plate 36 to oppose and to be spaced apart along the center axis 32 of the sensor casing 31 from the second inner surface 34 of the sensor casing 31 at a seventh space distance L7.

In this embodiment, the second space distance L2 is less than or equal to the diameter D1 of the third inner surface 35 of the sensor casing 31 multiplied by 0.1, and the seventh space distance L7 is less than or equal to the diameter D1 of the third inner surface 35 of the sensor casing 31 multiplied by 0.1.

The above description of the fourth embodiment has been made only about the oscillation plate 36 and the piezoelectric element 37 different from those of the third embodiment, but has not been directed to the sensor casing 31 and the supporting portion 51 which are entirely the same as those of the third embodiment. Detailed description about the sensor casing 31 and the supporting portion 51 will therefore be omitted hereinafter.

The fifth preferred embodiment of the acceleration sensor according to the present invention will now be described in detail in accordance with the accompanying drawings.

Figure 5:
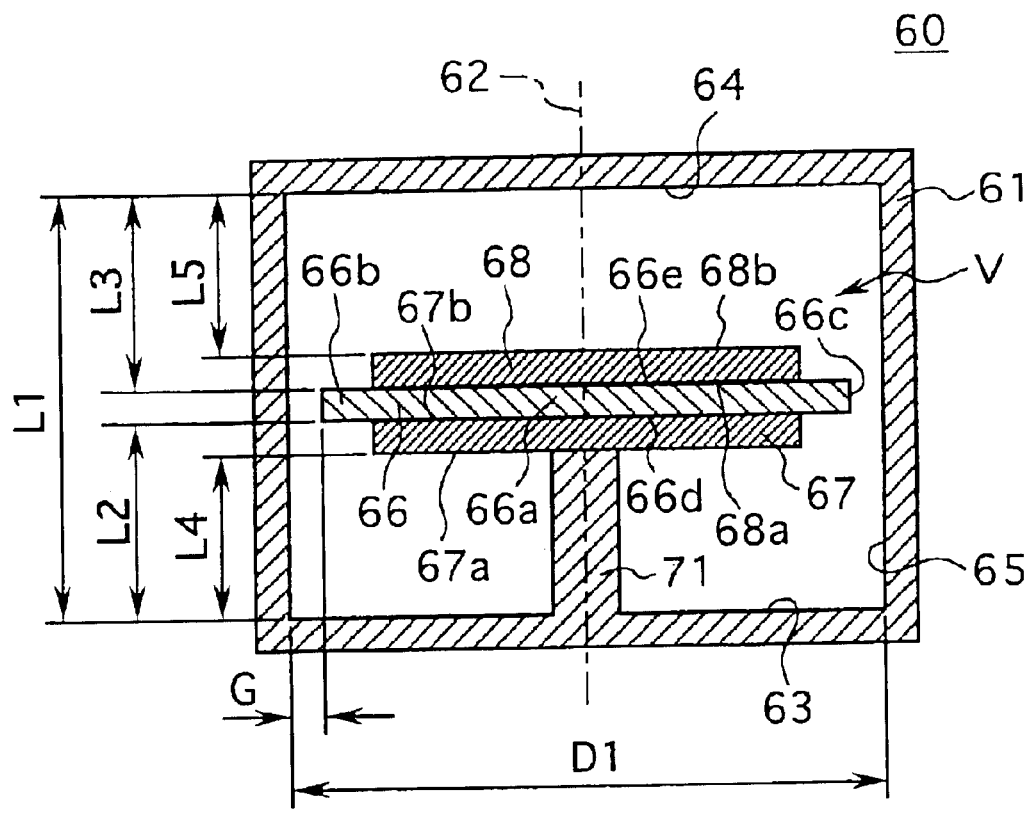
FIG. 5 is a cross-sectional view of the fifth embodiment of the acceleration sensor according to the present invention.

Referring now to the drawings, particularly to FIG. 5, the fifth preferred embodiment of the acceleration sensor is also assumed to be installed on an engine of an automotive vehicle in a similar fashion to the first to fourth embodiments. The acceleration sensor 60 comprises a sensor casing 61 having a center axis 62 and to be positioned in coaxial alignment with an oscillation direction to receive the acceleration. The sensor casing 61 has first and second circular inner surfaces 63 and 64 opposing to and spaced apart along the center axis 62 of the sensor casing 61 from each other at a first space distance L1, and a third cylindrical inner surface 65 connected at one end with the first inner surface 63 and at the other end with the second inner surface 64 to define a cylindrical closed space V.

The acceleration sensor 60 further comprises an oscillation plate 66 accommodated in the closed space V of the sensor casing 61. The oscillation plate 66 has a central portion 66a securely supported by the sensor casing 61, and a peripheral portion 66b integrally formed with the central portion 66a and extending radially outwardly of the central portion 66a to be freely movable with respect to the sensor casing 61. The oscillation plate 66 has a peripheral end surface 66c spaced apart from the third inner surface 65 of the sensor casing 61 at an annular gap G small enough to enable the oscillation plate 66 to oscillate with respect to the sensor casing 61. The oscillation plate 66 has a first flat surface 66d opposing to and spaced apart along the center axis 62 of the sensor casing 61 from the first inner surface 63 of the sensor casing 61 at a second space distance L2, and a second flat surface 66e opposing to and spaced apart along the center axis 62 of the sensor casing 61 from the second inner surface 64 of the sensor casing 61 at a third space distance L3.

The fact that the oscillation plate 66 has a peripheral portion 66b extending radially outwardly of the central portion 66a to be freely movable with respect to the sensor casing 61 leads to the fact that the oscillation plate 66 can be partly oscillated along the center axis 62 of the sensor casing 61 with respect to the sensor casing 61. With the oscillation of the oscillation plate 66, the oscillation plate 66 can be deformed.

The acceleration sensor 60 further comprises a first piezoelectric element 67 having first and second surfaces 67a and 67b and provided on the first flat surface 66d of the oscillation plate 66. The acceleration sensor 60 further comprises a second piezoelectric element 68 having first and second surfaces 68a and 68b and provided on the second flat surface 66e of the oscillation plate 66. The deformation of the peripheral portion 66b of the oscillation plate 66 causes the first and second piezoelectric elements 67 and 68 to generate a voltage indicative of the acceleration when the acceleration is exerted on the sensor casing 61 to have the oscillation plate 66 partly oscillated along the center axis 62 of the sensor casing 61 with respect to the sensor casing 61.

In the fifth embodiment of the acceleration sensor according to the present invention, the first space distance L1 is less than or equal to the diameter D1 of the third inner surface 65 of the sensor casing 61 multiplied by 0.1.

The sensor casing 61 has a supporting portion 71 projecting from the first inner surface 63 toward the second inner surface 64 to support the oscillation plate 66. The first piezoelectric element 67 is provided on the first flat surface 66d of the oscillation plate 66 to oppose and to be spaced apart along the center axis 62 of the sensor casing 61 from the first inner surface 63 of the sensor casing 61 at a fourth space distance L4. The second piezoelectric element 68 is provided on the second flat surface 66e of the oscillation plate 66 to oppose and to be spaced apart along the center axis 62 of the sensor casing 61 from the second inner surface 64 of the sensor casing 61 at a fifth space distance L5.

In this embodiment, the fourth space distance L4 is less than or equal to the diameter D1 of the third inner surface 65 of the sensor casing 61 multiplied by 0.1, and the fifth space distance L5 is less than or equal to the diameter D1 of the third inner surface 65 of the sensor casing 61 multiplied by 0.1.

The supporting portion 71 projecting from the first inner surface 63 toward the second inner surface 64 to support the oscillation plate 66 as shown in FIG. 5 may be replaced by a supporting portion projecting from the second inner surface 64 toward the first inner surface 63 to support the oscillation plate 66 according to the present invention.

Figure 6:
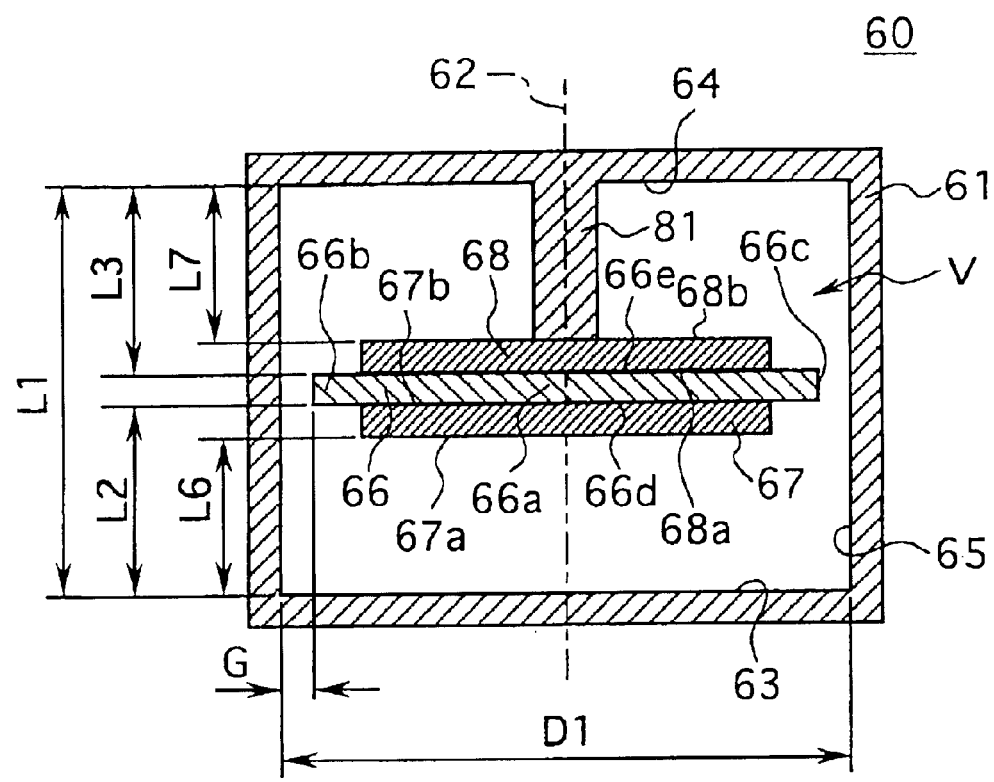
FIG. 6 is a cross-sectional view similar to FIG. 5 but showing the sixth embodiment of the acceleration sensor according to the present invention.

The sixth embodiment directed to the supporting portion projecting from the second inner surface 64 toward the first inner surface 63 to support the oscillation plate 66 is shown in FIG. 6.

In FIG. 6, the sensor casing 61 has a supporting portion 81 projecting from the second inner surface 64 toward the first inner surface 63 to support the oscillation plate 66. The first piezoelectric element 67 is provided on the first flat surface 66d of the oscillation plate 66 to oppose and to be spaced apart along the center axis 62 of the sensor casing 61 from the first inner surface 63 of the sensor casing 61 at a sixth space distance L6. The second piezoelectric element 68 is provided on the second flat surface 66e of the oscillation plate 66 to oppose and to be spaced apart along the center axis 62 of the sensor casing 61 from the second inner surface 64 of the sensor casing 61 at a seventh space distance L7.

In this embodiment, the sixth space distance L6 is less than or equal to the diameter D1 of the third inner surface 65 of the sensor casing 61 multiplied by 0.1, and the seventh space distance L7 is less than or equal to the diameter D1 of the third inner surface 65 of the sensor casing 61 multiplied by 0.1.

The above description of the sixth embodiment has been made only about the oscillation plate 66, the first piezoelectric element 67, the second piezoelectric element 68 and the supporting portion 81 different from those of the fifth embodiment, but has not been directed to the sensor casing 61 which is entirely the same as that of the fifth embodiment. Detailed description about the sensor casing 61 will therefore be omitted hereinafter.

Although the foregoing embodiments of the acceleration sensor described with reference to FIGS. 1 to 6 are concerned with the concept of the present invention, seventh and eighth embodiments are designed on the basis of the concept of the present invention to be practically available as will be seen from FIGS. 7 and 8.

Figure 7:
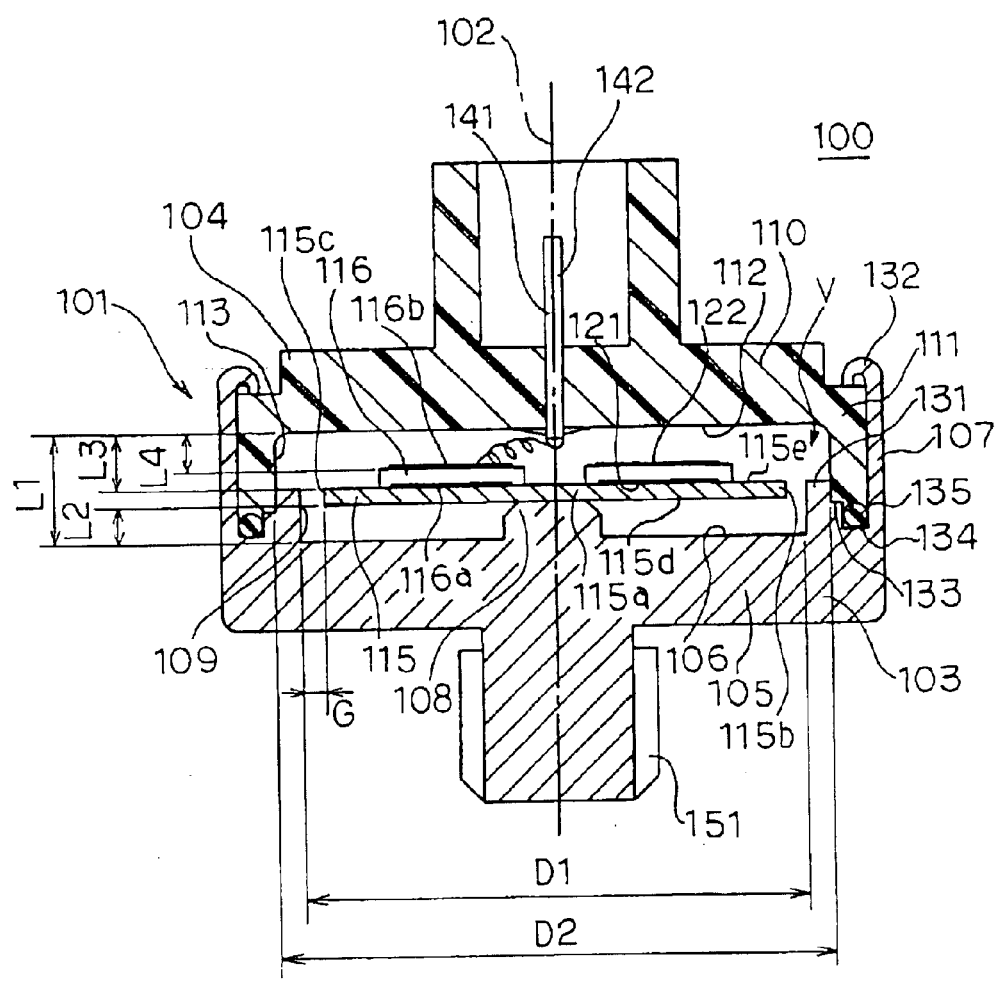
FIG. 7 is a cross-sectional view of the seventh embodiment of the acceleration sensor designed on the basis of the concept of the present invention to be practically available.

The seventh embodiment of the acceleration sensor for detecting the acceleration caused by the object oscillated in the oscillation direction is shown in FIG. 7 as comprising a sensor casing 101 having a center axis 102 and to be positioned in coaxial alignment with the oscillation direction to receive the acceleration. The sensor casing 101 includes a cylindrical fixed case member 103, and a cover member 104 provided on the fixed case member 103. The fixed case member 103 has a circular bottom portion 105 having a first circular inner surface 106, a cylindrical side portion 107 integrally formed with the bottom portion 105, and a supporting portion 108 projecting from the bottom portion 105. The side portion 107 of the fixed case member 103 has a third cylindrical inner surface 109 connected at one end with the first inner surface 106. The cover member 104 has a circular cover portion 110, and a cylindrical side portion 111 integrally formed with the cover portion 110. The cover portion 110 of the cover member 104 has a second circular inner surface 112 opposing to and spaced apart along the center axis 102 from the first inner surface 106 of the bottom portion 105 of the fixed case member 103 at a first space distance L1. The side portion 111 of the cover member 104 has a fourth cylindrical inner surface 113 connected at one end with the second inner surface 112. The first inner surface 106 of the bottom portion 105 of the fixed case member 103, the third inner surface 109 of the side portion 107 of the fixed case member 103, the second inner surface 112 of the cover portion 110 of the cover member 104 and the fourth inner surface 113 of the side portion 111 of the cover member 104 collectively define a cylindrical closed space V. As will be seen from FIG. 7, the diameter D1 of the third inner surface 109 of the side portion 107 of the fixed case member 103 is smaller than the diameter D2 of the fourth inner surface 113 of the side portion 111 of the cover member 104, however, the diameter D2 of the fourth inner surface 113 of the side portion 111 of the cover member 104 may be smaller than the diameter D1 of the third inner surface 109 of the side portion 107 of the fixed case member 103 according to the present invention.

The acceleration sensor further comprises an oscillation plate 115 accommodated in the closed space V of the sensor casing 101. The oscillation plate 115 has a central portion 115a securely supported by the supporting portion 108 of the fixed case member 103 of the sensor casing 101, and a peripheral portion 115b integrally formed with the central portion 115a and extending radially outwardly of the central portion 115a to be freely movable with respect to the sensor casing 101. The oscillation plate 115 has a peripheral end surface 115c spaced apart from the third inner surface 109 of the side portion 107 of the fixed case member 103 at an annular gap G small enough to enable the oscillation plate 115 to oscillate with respect to the sensor casing 101. According to the present invention, the third inner surface 109 of the side portion 107 of the fixed case member 103 may be replaced by the fourth inner surface 113 of the side portion 111 of the cover member 104. In short, the smaller one of the third and fourth inner surfaces 109 and 113 is required to be spaced apart from the peripheral end surface 115c of the oscillation plate 115 at an annular gap G small enough to enable the oscillation plate 115 to oscillate with respect to the sensor casing 101

The oscillation plate 115 has a first flat surface 115d opposing to and spaced apart along the center axis 102 from the first inner surface 106 of the bottom portion 105 of the fixed case member 103 at a second space distance L2 and a second flat surface 115e opposing to and spaced apart along the center axis 102 from the second inner surface 112 of the cover portion 110 of the cover member 104 at a third space distance L3. The fact that the oscillation plate 115 has a peripheral portion 115b extending radially outwardly of the central portion 115a to be freely movable with respect to the sensor casing 101 leads to the fact that the oscillation plate 115 can partly be oscillated along the center axis 102 of the sensor casing 101 with respect to the sensor casing 101. With the oscillation of the oscillation plate 115, the oscillation plate 115 can be deformed.

The acceleration sensor further comprises a piezoelectric element 116 having a first surface 116a held in contact with the second flat surface 115e of the oscillation plate 115, and a second surface 116b opposing to and spaced apart along the center axis 102 from the second inner surface 112 of the cover portion 110 of the cover member 104 at a fourth space distance L4. The piezoelectric element 116 is provided on the second flat surface 115e of the oscillation plate 115 in axial alignment with the oscillation plate 115. The deformation of the peripheral portion 115b of the oscillation plate 115 causes the piezoelectric element 116 to generate a voltage indicative of the acceleration when the acceleration is exerted on the sensor casing 101 to have the oscillation plate 115 partly oscillated along the center axis 102 with respect to the sensor casing 101.

In this embodiment, the first space distance L1 is less than or equal to the diameter D1 of the third inner surface 109 of the side portion 107 of the fixed case member 103 multiplied by 0.1, and the first space distance L1 is less than or equal to the diameter D2 of the fourth inner surface 113 of the side portion 111 of the cover member 104 multiplied by 0.1.

In this embodiment, the second space distance L2 is less than or equal to the diameter D1 of the third inner surface 109 of the side portion 107 of the fixed case member 103 multiplied by 0.1, and the fourth space distance L4 is less than or equal to the diameter D1 of the third inner surface 109 of the side portion 107 of the fixed case member 103 multiplied by 0.1

In this embodiment, the second space distance L2 is less than or equal to the diameter D2 of the fourth inner surface 113 of the side portion 111 of the cover member 104 multiplied by 0.1, and the fourth space distance L4 is less than or equal to the diameter D2 of the fourth inner surface 113 of the side portion 111 of the cover member 104 multiplied by 0.1.

The piezoelectric element 116 is in the form of an annular shape and has the first surface 116a held in contact with the second flat surface 115e of the oscillation plate 115 and having thereon a first electrode 121 between the first surface 116a of the piezoelectric element 116 and the second flat surface 115e of the oscillation plate 115, and the second surface 116b opposing to the second inner surface 112 of the cover portion 110 of the cover member 104 and having thereon a second electrode 122 opposing to the second inner surface 112 of the cover portion 110 of the cover member 104. The first and second electrodes 121 and 122 enable the voltage indicative of the acceleration to output therethrough.

The fixed case member 103 is made of a metal, and the cover member 104 is made of a plastic:

The side portion 107 of the fixed case member 103 has a first section 131 close to the bottom portion 105 of the fixed case member 103, a second section 132 remote from the bottom portion 105 of the fixed case member 103, and an annular ledge section 133 formed between the first and second sections 131 and 132 with an annular groove 134 open toward the side portion 111 of the cover member 104.

The diameter D1 of the first section 131 of the side portion 107 of the fixed case member 103 is smaller than the diameter D2 of the side portion 111 of the cover member 104. The side portion 111 of the cover member 104 is snugly received in the annular groove 134 with a resilient ring 135 intervening between the annular ledge section 133 of the side portion 107 of the fixed case member 103 and the side portion 111 of the cover member 104 to hermetically seal the gap between the annular ledge section 133 of the side portion 107 of the fixed case member 103 and the side portion 111 of the cover member 104.

The acceleration sensor further comprises an output terminal pin 141 mounted on the cover member 104 and extending into the closed space V to be electrically connected to the piezoelectric element 116. The output terminal pin 141 has a terminal end portion 142 projecting outwardly of the cover member 104 and electrically connectable with an exterior coupling member to output the voltage indicative of the acceleration.

The fixed case member 103 has a screw portion 151 to be screwed to the object which is to receive the acceleration.

The supporting portion 108 of the fixed case member 103 projects toward the cover portion 110 of the cover member 104 and is tapered toward the oscillation plate 115.

Figure 8:
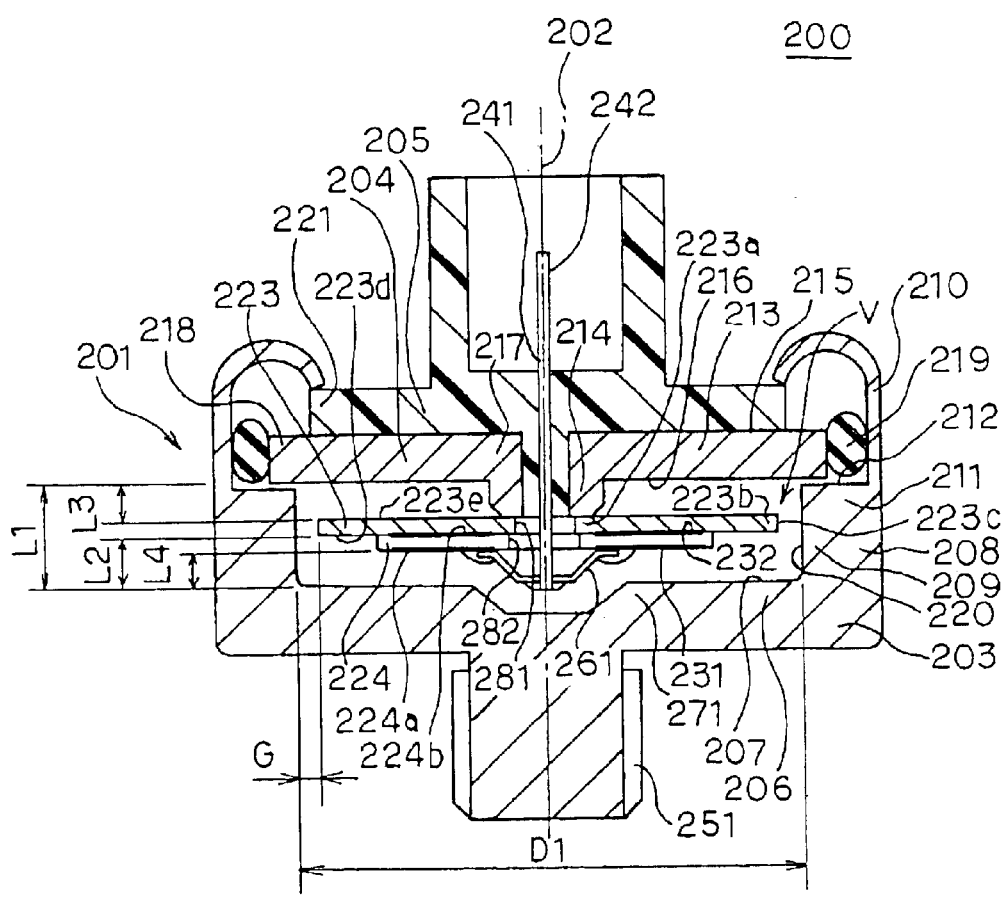
FIG. 8 is a cross-sectional view of the eighth embodiment of the acceleration sensor designed on the basis of the concept of the present invention to be practically available.

The eighth embodiment of the acceleration sensor for detecting the acceleration caused by the object oscillated in the oscillation direction is shown in FIG. 8 as comprising a sensor casing 201 having a center axis 202 and to be positioned in coaxial alignment with the oscillation direction to receive the acceleration. The sensor casing 201 includes a cylindrical fixed case member 203, a metal base member 204 mounted on the fixed case member 203, and a cover member 205 provided on the metal base member 204. The fixed case member 203 of the sensor casing 201 has a circular bottom portion 206 having a first circular inner surface 207, and a cylindrical side portion 208 integrally formed with the bottom portion 206. The side portion 208 of the fixed case member 203 has a first section 209 close to the bottom portion 206 of the fixed case member 203, a second section 210 remote from the bottom portion 206 of the fixed case member 203 and radially inwardly bent, and an annular ledge section 211 formed between the first and second sections 209 and 210 with an annular ledge 212. The metal base member 204 of the sensor casing 201 has a circular base portion 213 and a supporting portion 214. The base portion 213 of the metal base member 204 has a circular outer surface 215, and a second circular inner surface 216 opposing to and spaced apart along the center axis 202 from the first inner surface 207 of the bottom portion 206 of the fixed case member 203 at a first space distance L1. The supporting portion 214 of the metal base member 204 projects from the second inner surface 216 of the base portion 213 of the metal base member 204. The base portion 213 of the metal base member 204 has a central section 217 integrally formed with the supporting portion 214 of the metal base member 204, and a peripheral section 218 integrally formed with the central section 217 and extending radially outwardly of the central section 217. The metal base member 204 is mounted on the annular ledge 212 of the fixed case member 203 with a resilient ring 219 intervening between the second section 210 of the side portion 208 of the fixed case member 203 and the peripheral section 218 of the base portion 213 of the metal base member 204 to hermetically seal the gap between the second section 210 of the side portion 208 of the fixed case member 263 and the peripheral section 218 of the base portion 213 of the metal base member 204. The first section 209 of the side portion 208 of the fixed case member 203 has a third cylindrical inner surface 220 connected at one end with the first inner surface 207 of the bottom portion 206 of the fixed case member 203 and at the other end with the second inner surface 216 of the base portion 213 of the metal base member 204. The cover member 205 of the sensor casing 201 is provided on the outer surface 215 of the metal base member 204 and has a peripheral section 221 firmly engaged with the second section 210 of the side portion 208 of the fixed case member 203. The first inner surface 207 of the bottom portion 206 of the fixed case member 203, the second inner surface 216 of the base portion 213 of the metal base member 204, and the third inner surface 220 of the first section 209 of the side portion 208 of the fixed case member 203 collectively define a cylindrical closed space V.

The acceleration sensor 200 further comprises an oscillation plate 223 accommodated in the closed space V of the sensor casing 201; The oscillation plate 223 has a central portion 223a securely supported by the supporting portion 214 of the metal base member 204 of the sensor casing 201, and a peripheral portion 223b integrally formed with the central portion 223a and extending radially outwardly of the central portion 223a to be freely movable with respect to the sensor casing 201. The oscillation plate 223 has a peripheral end surface 223c spaced apart from the third inner surface 220 of the first section 209 of the side portion 208 of the fixed case member 203 at an annular gap G small enough to enable the oscillation plate 223 to oscillate with respect to the sensor casing 201.

The oscillation plate 223 has a first flat surface 223d opposing to and spaced apart along the center axis 202 from the first inner surface 207 of the bottom portion 206 of the fixed case member 203 at a second space distance L2 and a second flat surface 223e opposing to and spaced apart along the center axis 202 from the second inner surface 216 of the base portion 213 of the metal base member 204 at a third space distance L3. The fact that the oscillation plate 223 has a peripheral portion 223b extending radially outwardly of the central portion 223a to be freely movable with respect to the sensor casing 201 leads to the fact that the oscillation plate 223 can partly be oscillated along the center axis 202 of the sensor casing 201 with respect to the sensor casing 201. With the oscillation of the oscillation plate 223, the oscillation plate 223 can be deformed.

The acceleration sensor 200 further comprises a piezoelectric element 224 having a first surface 224a opposing to and spaced apart along the center axis 202 from the first inner surface 207 of the bottom portion 206 of the fixed case member 203 at a fourth space distance L4, and a second surface 224b held in contact with the first flat surface 223d of the oscillation plate 223. The piezoelectric element 224 is provided on the first flat surface 223d of the oscillation plate 223 in axial alignment with the oscillation plate 223. The deformation of the peripheral portion 223b of the oscillation plate 223 causes the piezoelectric element 224 to generate a voltage indicative of the acceleration when the acceleration is exerted on the sensor casing 201 to have the oscillation plate 223 partly oscillated along the center axis 202 with respect to the sensor casing 201.

In this embodiment, the first space distance L1 is less than or equal to the diameter D1 of the third inner surface 220 of the first section 209 of the side portion 208 of the fixed case member 203 multiplied by 0.1.

In this embodiment, the third space distance L3 is less than or equal to the diameter D1 of the third inner surface 220 of the first section 209 of the side portion 208 of the fixed case member 203 multiplied by 0.1, and the fourth space distance L4 is less than or equal to the diameter D1 of the third inner surface 220 of the first section 209 of the side portion 208 of the fixed case member 203 multiplied by 0.1.

The piezoelectric element 224 is in the form of an annular shape and has the first surface 224a opposing to the first inner surface 207 of the bottom portion 206 of the fixed case member 203 and having thereon a first electrode 231 opposing to the first inner surface 207 of the bottom portion 206 of the fixed case member 203, and the second surface 224b held in contact with the first flat surface 223d of the oscillation plate 223 and having thereon a second electrode 232 between the second surface 224b of the piezoelectric element 224 and the first flat surface 223d of the oscillation plate 223. The first and second electrodes 231 and 232 enable the voltage indicative of the acceleration to output therethrough.

The fixed case member 203 and the metal base member 204 are made of a metal, and the cover member 205 is made of a plastic.

The acceleration sensor 200 further comprises an output terminal pin 241 mounted on the cover member 205 and partly extending through the cover member 205, the supporting portion 214 of the metal base member 204, the oscillation plate 223, and the piezoelectric element 224 into the closed space V to be electrically connected to the piezoelectric element 224. The output terminal pin 241 has a terminal end portion 242 projecting outwardly of the cover member 205 and electrically connectable with an exterior coupling member to output the voltage indicative of the acceleration.

The fixed case member 203 has a screw portion 251 to be screwed to the object which is to receive the acceleration.

The supporting portion 214 of the metal base member 204 projects toward the bottom portion 206 of the fixed case member 203 and is tapered toward the oscillation plate 223 and formed with a through bore.

The acceleration sensor 200 further comprises a resilient metal plate 261 in the form of a truncated cone shape and having an open end electrically connectable with the piezoelectric element 224.

The bottom portion 206 of the fixed case member 203 is formed with a central cavity plate 271 open toward the metal plate 261 and in the form similar to the shape of the metal plate 261.

The oscillation plate 223 has a central hole 281 formed at the center portion thereof and open at the first and second flat surfaces 223d and 223e. The piezoelectric element 224 has a central hole 282 formed at the center portion thereof and open at its first and second surfaces 224a and 224b.

Although the foregoing embodiments of the acceleration sensor described with reference to FIGS. 7 and 8 are designed on the basis of the concept of the present invention to be practically available, the foregoing embodiments of the acceleration sensor may be replaced by a ninth embodiment designed on the basis of another concept of the present invention to be practically available as will be seen from FIG. 9.

Figure 9:
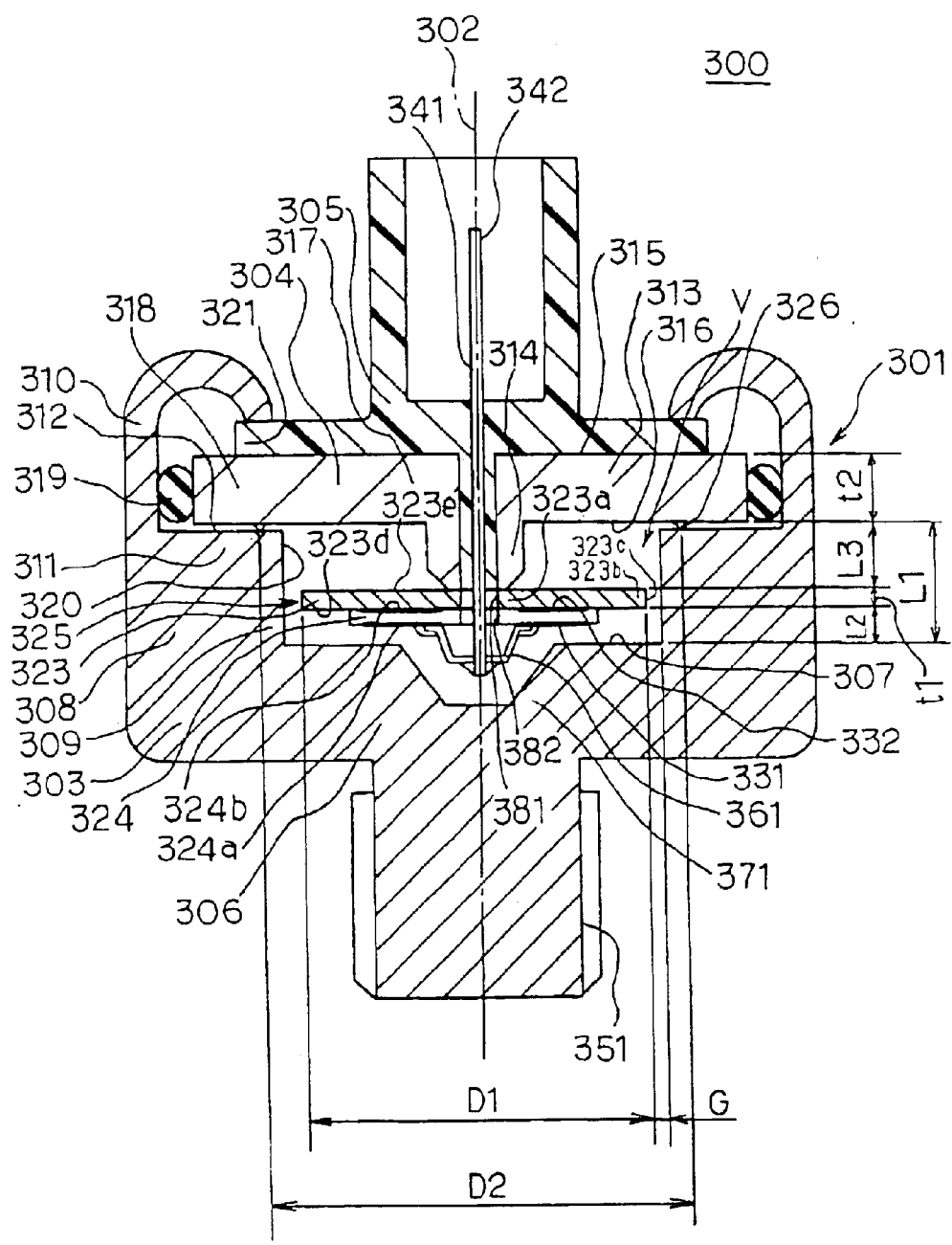
FIG. 9 is a cross-sectional view of the ninth embodiment of the acceleration sensor designed on the basis of the concept of the present invention to be practically available.

The ninth embodiment of the acceleration sensor for detecting an acceleration caused by the object oscillated in the oscillation direction is shown in FIG. 9 as comprising a sensor casing 301 having a center axis 302 and to be positioned in coaxial alignment with the oscillation direction to receive the acceleration. The sensor casing 301 includes a cylindrical fixed case member 303, a metal base member 304 mounted on the fixed case member 303, and a cover member 305 provided on the metal base member 304. The fixed case member 303 of the sensor casing 301 has a circular bottom portion 306 having a first circular inner surface 307, and a cylindrical side portion 308 integrally formed with the bottom portion 306. The side portion 308 of the fixed case member 303 has a first section 309 close to the bottom portion 306 of the fixed case member 303, a second section 310 remote from the bottom portion 306 of the fixed case member 303 and radially inwardly bent, and an annular ledge section 311 formed between the first and second sections 309 and 310 with an annular ledge 312. The metal base member 304 of the sensor casing has a circular base portion 313 and a supporting portion 314. The base portion 313 of the metal base member 304 has a circular outer surface 315, and a second circular inner surface 316 opposing to and spaced apart along the center axis 302 from the first inner surface 307 of the bottom portion 306 of the fixed case member 303 at a first space distance L1. The supporting portion 314 of the metal base member 304 projects from the second inner surface 316 of the base portion 313 of the metal base member 304. The base portion 313 of the metal base member 304 has a central section 317 integrally formed with the supporting portion 314 of the metal base member 304, and a peripheral section 318 integrally formed with the central section 317 and extending radially outwardly of the central section 317. The metal base member 304 is mounted on the annular ledge 312 of the fixed case member 303 with a resilient ring 319 intervening between the second section 310 of the side portion 308 of the fixed case member 303 and the peripheral section 318 of the base portion 313 of the metal base member 304 to hermetically seal the gap between the second section 310 of the side portion 308 of the fixed case member 303 and the peripheral section 318 of the base portion 313 of the metal base member 304. The first section 309 of the side portion 308 of the fixed case member 303 has a third cylindrical inner surface 320 connected at one end with the first inner surface 307 of the bottom portion 306 of the fixed case member 303 and at the other end with the second inner surface 316 of the base portion 313 of the metal base member 304. The cover member 305 of the sensor casing 301 is provided on the outer surface 315 of the metal base member 304 and has a peripheral section 321 firmly engaged with the second section 310 of the side portion 308 of the fixed case member 303. The first inner surface 307 of the bottom portion 306 of the fixed case member 303, the second inner surface 316 of the base portion 313 of the metal base member 304, and the third inner surface 320 of the first section 309 of the side portion 308 of the fixed case member 303 collectively define a cylindrical closed space V.

The acceleration sensor 300 further comprises an oscillation plate 323 accommodated in the closed space V of the sensor casing 301. The oscillation plate 323 has a central portion 323a securely supported by the supporting portion 314 of the metal base member 304 of the sensor casing 301, and a peripheral portion 323b integrally formed with the central portion 323a and extending radially outwardly of the central portion 323a to be freely movable with respect to the sensor casing 301. The oscillation plate 323 has a peripheral end surface 323c spaced apart from the third inner surface 320 of the first section 309 of the side portion 308 of the fixed case member 303 at an annular gap G small enough to enable the oscillation plate 323 to oscillate with respect to the sensor casing 301.

The oscillation plate 323 has a first flat surface 323d opposing to and spaced apart along the center axis 302 from the first inner surface 307 of the bottom portion 306 of the fixed case member 303 at a second space distance L2 and a second flat surface 323e opposing to and spaced apart along the center axis 302 from the second inner surface 316 of the base portion 313 of the metal base member 304 at a third space distance L3. The fact that the oscillation plate 323 has a peripheral portion 323b extending radially outwardly of the central portion 323a to be freely movable with respect to the sensor casing 301 leads to the fact that the oscillation plate 323 can partly be oscillated along the center axis 302 of the sensor casing 301 with respect to the sensor casing 301. With the oscillation of the oscillation plate 323, the oscillation plate 323 can be deformed.

The acceleration sensor 300 further comprises a piezoelectric element 324 having first and second surfaces 324a and 324b and provided on at least one of the first and second flat surfaces 323d and 323e of the oscillation plate 323 in axial alignment with the oscillation plate 323. The deformation of the peripheral portion 323b of the oscillation plate 323 causes the piezoelectric element 324 to generate a voltage indicative of the acceleration when the acceleration is exerted on the sensor casing 301 to have the oscillation plate 323 partly oscillated along the center axis 302 with respect to the sensor casing 301. The oscillation plate 323 and the piezoelectric element 324 collectively constitute an oscillation body 325.

In this embodiment, the resonance frequency of the sensor casing 301 is more than or equal to the resonance frequency of the oscillation body 325 multiplied by 3.

In this embodiment, the modulus of elasticity in bending of the cover member 305 is more than or equal to $8 \times 10^3$ (MPa), and the logarithmic decrement of the cover member 305 is more than or equal to 8 (1/s).

In this embodiment, the fixed case member 303 and the metal base member 304 are made of a metal, and the cover member 305 is made of a polymer liquid crystal.

The metal base member 304 has a circumferential section 326 firmly connected to the annular ledge section 311 of the side portion 308 of the fixed case member 303.

In this embodiment, the diameter D2 of the circumferential section 326 of the metal base member 304 is less than or equal to the diameter D1 of the oscillation plate 323 multiplied by 1.4, and the thickness t2 of the metal base member 304 is more than or equal to the thickness t1 of the oscillation plate 323 multiplied by 6.

The piezoelectric element 324 is in the form of an annular shape and provided on the first flat surface 323d of the oscillation plate 323. The piezoelectric element 324 has the first surface 324a opposing to the first inner surface 307 of the bottom portion 306 of the fixed case member 303 and having thereon a first electrode 331 opposing to the first inner surface 307 of the bottom portion 306 of the fixed case member 303, and the second surface 324b held in contact with the first flat surface 323d of the oscillation plate 323 and having thereon a second electrode 332 between the second surface 324b of the piezoelectric element 324 and the first flat surface 323d of the oscillation plate 323. The first and second electrodes 331 and 332 enable the voltage indicative of the acceleration to output therethrough.

The acceleration sensor 300 further comprises an output terminal pin 341 mounted on the cover member 305 and partly extending through the cover member 305, the supporting portion 314 of the metal base member 304, the oscillation plate 323, and the piezoelectric element 324 into the closed space V to be electrically connected to the piezoelectric element 324. The output terminal pin 341 has a terminal end portion 342 projecting outwardly of the cover member 305 and electrically connectable with an exterior coupling member to output the voltage indicative of the acceleration.

The fixed case member 303 has a screw portion 351 to be screwed to the object which is to receive the acceleration.

The supporting portion 314 of the metal base member 304 projects toward the bottom portion 306 of the fixed case member 303 and is tapered toward the oscillation plate 323 and formed with a through bore.

The acceleration sensor 300 further comprises a resilient metal plate 361 in the form of a truncated cone shape and having an open end electrically connectable with the piezoelectric element 324.

The bottom portion 306 of the fixed case member 303 is formed with a central cavity plate 371 open toward the metal plate 361 and in the form similar to the shape of the metal plate 361.

The oscillation plate 323 has a central hole 381 formed at the center portion thereof and open at the first and second flat surfaces 323d and 323e. The piezoelectric element 324 has a central hole 382 formed at the center portion thereof and open at its first and second surfaces 324a and 324b.

The piezoelectric element 324 provided on the first flat surface 323d of the oscillation plate 323 as shown in FIG. 9 may be replaced by a piezoelectric element provided on the second flat surface 323e of the oscillation plate 323 according to the present invention.

The tenth embodiment directed to the piezoelectric element provided on the second flat surface 323e of the oscillation plate 323 is shown in FIG. 10.

In FIG. 10, the acceleration sensor 300 further comprises a piezoelectric element 324 having first and second surfaces 324a and 324b and provided on at least one of the first and second flat surfaces 323d and 323e of the oscillation plate 323 in axial alignment with the oscillation plate 323. The deformation of the peripheral portion 323b of the oscillation plate 323 causes the piezoelectric element 324 to generate a voltage indicative of the acceleration when the acceleration is exerted on the sensor casing 301 to have the oscillation plate 323 partly oscillated along the center axis 302 with respect to the sensor casing 301. The oscillation plate 323 and the piezoelectric element 324 collectively constitute an oscillation body 325.

The piezoelectric element 324 is in the form of an annular shape and provided on the second flat surface 323e of the oscillation plate 323. The piezoelectric element 324 has the first surface 324a held in contact with the second flat surface 323e of the oscillation plate 323 and having thereon a first electrode 331 between the first surface 324a of the piezoelectric element 324 and the second flat surface 323e of the oscillation plate 323, and the second surface 324b opposing to the second inner surface 316 of the base portion 313 of the metal base member 304 and having thereon a second electrode 332 opposing to the second inner surface 316 of the base portion 313 of the metal base member 304. The first and second electrodes 331 and 332 enable the voltage indicative of the acceleration to output therethrough.

The piezoelectric element 324 provided on at least one of the first and second flat surfaces 323d and 323e of the oscillation plate 323 as shown in FIGS. 9 and 10 may be replaced by piezoelectric elements respectively provided on the first and second flat surfaces 323d and 323e of the oscillation plate 323 according to the present invention.

Figure 11:
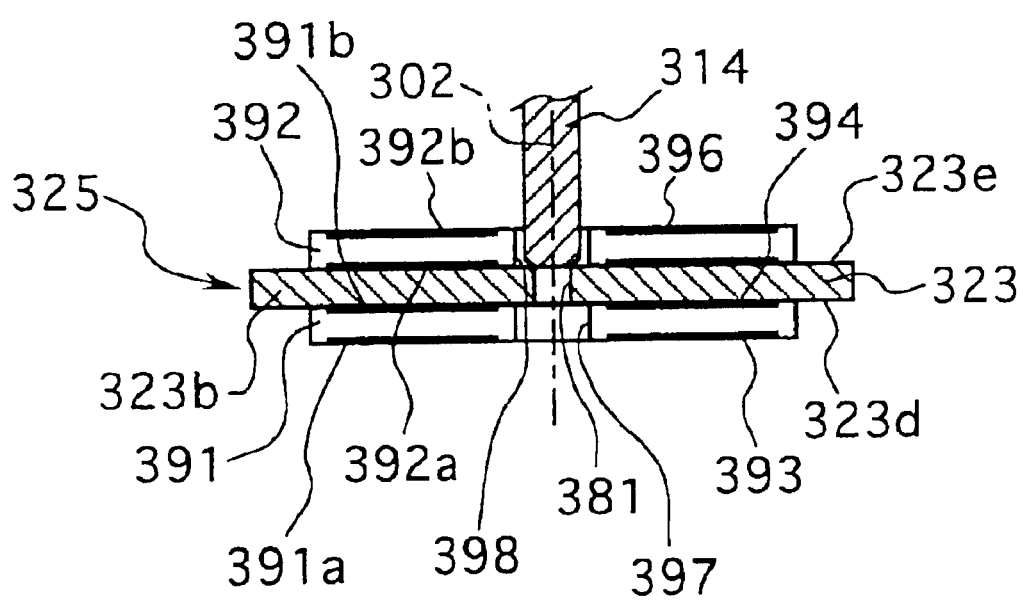
FIG. 11 is an enlarged and fragmentary cross-sectional view of the acceleration sensor shown in FIG. 9.

The eleventh embodiment directed to the piezoelectric elements provided on both of the first and second flat surfaces 323d and 323e of the oscillation plate 323 is shown in FIG. 11.

In FIG. 11, the acceleration sensor 300 further comprises a first piezoelectric element 391 having first and second surfaces 391a and 391b and provided on the first flat surface 323d of the oscillation plate 323 in axial alignment with the oscillation plate 323, and a second piezoelectric element 392 having first and second surfaces 392a and 392b and provided on the second flat surface 323e of the oscillation plate 323 in axial alignment with the oscillation plate 323. The deformation of the peripheral portion 323b of the oscillation plate 323 causes the first and second piezoelectric elements 391 and 392 to generate a voltage indicative of the acceleration when the acceleration is exerted on the sensor casing 301 to have the oscillation plate 323 partly oscillated along the center axis 302 with respect to the sensor casing 301. The oscillation plate 323 and the first and second piezoelectric elements 391 and 392 collectively constitute an oscillation body 325.

The first piezoelectric element 391 is in the form of an annular shape and provided on the first flat surface 323d of the oscillation plate 323. The first piezoelectric element 391 has the first surface 391a opposing to the first inner surface 307 of the bottom portion 306 of the fixed case member 303 and having thereon a first electrode 393 opposing to the first inner surface 307 of the bottom portion 306 of the fixed case member 303, and the second surface 391b held in contact with the first flat surface 323d of the oscillation plate 323 and having thereon a second electrode 394 between the second surface 391b of the first piezoelectric element 391 and the first flat surface 323d of the oscillation plate 323. The first and second electrodes 393 and 394 of the first piezoelectric element 391 enable the voltage indicative of the acceleration to output therethrough.

The second piezoelectric element 392 is in the form of an annular shape and provided on the second flat surface 323e of the oscillation plate 323. The second piezoelectric element 392 has the first surface 392a held in contact with the second flat surface 323e of the oscillation plate 323 and having thereon a first electrode 395 between the first surface 392a of the second piezoelectric element 392 and the second flat surface 323e of the oscillation plate 323, and the second surface 392b opposing to the second inner surface 316 of the base portion 313 of the metal base member 304 and having thereon a second electrode 396 opposing to the second inner surface 316 of the base portion 313 of the metal base member 304. The first and second electrodes 395 and 396 of the second piezoelectric element 392 enable the voltage indicative of the acceleration to output therethrough.

The first piezoelectric element 391 has a central hole 397 formed at the center portion thereof and open at its first and second surfaces 391a and 391b. The second piezoelectric element 392 has a central hole 398 formed at the center portion thereof and open at its first and second surfaces 392a and 392b.

The effect and advantage of the present invention will be described hereinafter in association with the dimensions of the constitution elements forming the seventh and eighth embodiments of the acceleration sensor according to the present invention.

Figure 12:
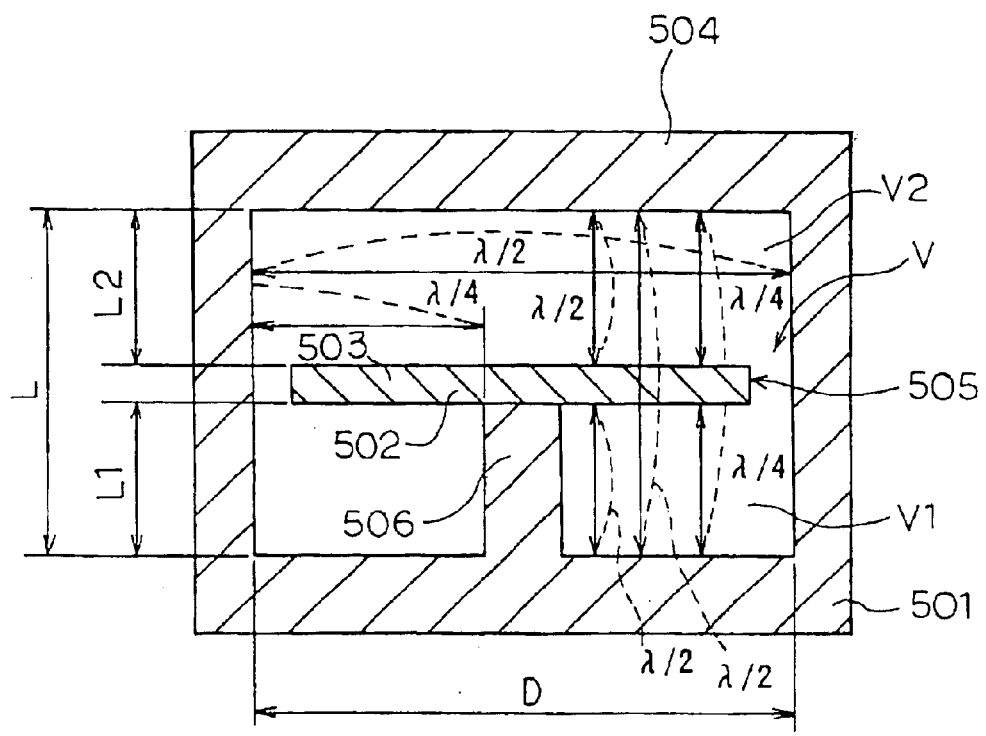
FIG. 12 is a cross-sectional view of a model for explaining the generation of the standing wave.

FIG. 12 shows a roughly drawn modeled example which comprises a fixed case member 501, an oscillation plate 502, a piezoelectric element 503, and a cover member 504 in a similar fashion to the foregoing embodiments. The oscillation plate 502 and the piezoelectric element 503 collectively constitute an oscillation body 505 which is accommodated in a closed space V defined by the fixed case member 501 and the cover member 504. The closed space V is divided into two space sections V1 and V2 by the oscillation body 505. Assuming that the acceleration sensor 500 is mounted for example on the automotive engine to have the oscillation body 505 oscillated with respect to the fixed case member 501 and the cover member 504, the oscillation of the oscillation body 505 causes sound and thus serves as a sound source. The sound thus caused by oscillation of the oscillation body 505 is apt to generate in the closed space V a standing wave which is one kind of sound waves looking as if it is at a standstill.

In general, such a standing wave is generated at a sound source which is provided in a closed space like the above closed space V and in a partly open space, for example, defined by a tube having an end open to the outside thereof. The standing wave is usually produced by two directionally opposite waves of the same frequency overlaid on each other and thus consists of a progressive wave having a frequency, and a reflected wave having the same frequency as that of the progressive wave and overlaid when the progressive wave strikes some object and bounces back from the object. The standing wave has a maximum point at its maximum amplitude, and a zero point at its zero amplitude. Further, the standing wave has a wide variety of complicated forms differing depending upon the materials, the contours of the walls forming the closed space V and other factors. The standing wave is extremely difficult to analyze but the frequency fc of the standing wave is generally given by the following equation, $$fc = u/\lambda$$

wherein u is sonic speed (m/s), and $\lambda$ is wave length (m).

From this equation, it is found that the standing wave is generated at whole number times the frequency fc of the standing wave that is in proportion to the sonic speed u.

The standing wave in the acceleration sensor 500 is generated under two conditions consisting of a first condition that length b of the acceleration sensor 500 is equal to $\lambda/2$ for the acceleration sensor 500 having the closed space V as in the example described in the above, and a second condition that length b of the acceleration sensor 500 is equal to $\lambda/4$ for the acceleration sensor 500 having one end open to the outside thereof. The frequencies fc of the standing waves to be generated respectively in the above two types of the acceleration sensor 500 is therefore given by the following equations $$fc = u/(2 \times b) \quad (1)$$

$$fc = u/(4 \times b) \quad (2)$$

wherein the equation (1) is applied for the acceleration sensor 500 having a closed space V, while the equation (2) is applied for the acceleration sensor 500 having one end open to the outside thereof. Incidentally, in the event that the walls forming the acceleration sensor 500 are each made of a material extremely high in sound absorptive power, the standing wave is generated with the length b of the acceleration sensor 500 being equal to $\lambda/4$ even if the acceleration sensor 500 has the closed space V as in the example described in the above. The legend b herein used represents the height L of the closed space V or the diameter D of the closed space V as shown in FIG. 12. For this reason, there appears no legend referring to b.

In view of the above principle, the acceleration sensor 500 should be designed to have the standing wave in the closed space V generated out of the usable frequency range within which the acceleration sensor 500 is used, or otherwise to have the walls surrounding the closed space V made of a material absorptive to the sound generated by the oscillation of the oscillation body 505. The outside of the usable frequency range here raised generally indicates the outside of the upper limit of the usable frequency range. The material absorptive to the sound affects an acoustic resistance that is intended to mean "sound spreading degree" or "sound transmission restraining degree". It is therefore understood that the high acoustic resistance is representative of a high difficulty rate to transmit a sound, while the low acoustic resistance is indicative of a high easiness rate to transmit a sound. This means that the sound absorption material serves to increase the levels of the acoustic resistance. As will be seen from the foregoing description, the design of the acceleration sensor 500 is made in consideration of preventing the standing wave generated therein by the methods of (1) having the standing wave generated out of the usable frequency range of the acceleration sensor 500, and (2) raising the acoustic resistance.

If the frequency fo of the acceleration sensor 500 is generally used in the range below 20 (kHz), the frequency fo of the standing wave is required to be above 20 (kHz). Taking FIG. 12 for example, the following description will be focused on the frequency of the standing wave in the acceleration sensor 500 based on our experimental study attempted to make the frequency fo of the standing wave forced out from the usable frequency range of the acceleration sensor 500. The standing wave taken in this instance shown in FIG. 12 is generated in the oscillation direction of the oscillation plate 502. i.e., in the direction along the height L of the closed space V. Among other things, the above experimental study has been conducted with the walls of the acceleration sensor 500 made of no sound absorption material.

The standing wave of the lowest frequency in the direction along the height L of the closed space V is generated when the height L is equal to $\lambda/2$. The lowest frequency of the standing wave is varied in response to the material available for the walls of the acceleration sensor 500 as well as to the position of the sound source close to the open end of the closed space V. The standing wave of the lowest frequency is generated at the height L equal to $\lambda/4$ when the material available for the walls of the acceleration sensor 500 and the position of the sound source close to the open end of the closed space V come to be coincident to the respective optimum values. From the above equations (1) and (2) are given following heights L if u is 343.59 (m) and fo is 20 (kHz). The heights L are practical and can prevent the standing wave from being generated in the direction along the height L of the closed space V in a relatively easy way.

L≦8.59 (mm) for λ/2
L≦4.29 (mm) for λ/4

On the other hand, the standing wave generated in the direction along the diameter D of the closed space V is varied in response to the size of the diameter D of the closed space V. i.e., the size of the diameter D of the closed space V formed by the fixed case member 501 and the cover member 504. The frequency fo of the acceleration sensor 500 is generally used in the range above 6 to 7 (kHz). The lowest frequency fo of the acceleration sensor 500 is decided based on the thickness and diameter of the oscillation body 505 and the material of the oscillation body 505. The thickness and diameter of the oscillation body 505 thus decided make it easy to decide the diameter D of the inner surface of the fixed case member 501 by the reason that the gap between the inner surface of the fixed case member 501 and the peripheral end of the oscillation body 505 is formed small enough to enable the oscillation body 505 to be oscillated with respect to the fixed case member 501. Under the following conditions, the lowest frequency fo of the acceleration sensor 500 is set at about 7.095 (kHz).

<Supporting Portion 506>
diameter: φ4.3 (mm)
<Oscillation Plate 502>
outer diameter/inner diameter: φ21.6/3.1 (mm)
thickness: 0.4 (mm)
modulus of elasticity E: $2\times10^{11}$ (N/m$^2$)
density ρ: $7.8\times10^3$ (kg/m$^3$)
Poisson's ratio σ: 0.28
<Piezoelectric Element 503>
outer diameter/inner diameter: φ15.8/3.1 (mm)
thickness: 0.38 (mm)
modulus of elasticity E: $6.3\times10^{10}$ (N/m$^2$)
density ρ: $7.65.\times10^3$ (kg/m$^3$)
Poisson's ratio σ: 0.34

The diameter D of the inner surface of the fixed case member 501 is decided based on the outer diameter of the oscillation plate 502. In the present example, the diameter D of the inner surface of the fixed case member 501 is set at about 23 (mm) in order to avoid the acceleration sensor 500 from becoming extremely large in size. The frequency of the standing wave is about 7.47 (kHz) as the diameter D is λ/2. The standing wave is likely to be generated in the usable range of the acceleration sensor 500.

From the above fact, it is required to set a relatively large acoustic resistance in the closed space V for the purpose of preventing the standing wave from being generated in the direction along the diameter D of the inner surface of the fixed case member 501. In order to set the relatively large acoustic resistance without any sound absorption material used for the walls of the fixed case member 501, it is considered to take advantage of a viscosity resistance in air.

Taking an air layer for example, its acoustic resistance y is represented by the following equation.

$$\gamma = 12 \times \mu \times d/(w \times h^3)$$

μ: viscosity resistance of air
d: length of air layer
w: width of air layer
h: height of air layer It is found from the above equation that the height h of air layer is effectively reduced to be small for the large acoustic resistance γ. This option is most preferable to prevent the standing wave from being generated in the direction along the height L of the closed space V.

The distance L1 between the lower surface of the oscillation body 505 and the upper surface of the bottom portion of the fixed case member 501, and the distance L2 between the upper surface of the oscillation body 505 and the lower surface of the cover member 504 in FIG. 12 are selected based on the experimental results in view of the standing wave which is not generated. The distances L1 and L2 selected in this way are preferably below about 0.1 times the diameter D of the inner surface of the fixed case member 501. The closed space section V2 between the upper surface of the oscillation body 505 and the lower surface of the cover member 504 is more influential to the generation of the standing wave than the closed space section V1 between the lower surface of the oscillation body 505 and the upper surface of the bottom portion of the fixed case member 501. The reason is considered to be due to the fact that the supporting portion 506 is positioned in the closed section V1.

The lower limits of the distances L1 and L2 are preferably set at respective dimensions small enough to allow the oscillation body 505 to oscillate with respect to the fixed case member 501 and the cover member 504.

Under the state that the diameter D is 23 (mm), the distances L1 and L2 are respectively less than or equal to 2.3 (mm). Under the state that the diameter D is 19 (mm), the distances L1 and L2 are respectively less than or equal to 1.9 (mm). Based on the previous conditions, the acceleration sensor 500 having the closed space V is designed to prevent the standing wave in the direction along the diameter D of the inner surface of the fixed case member 501. On the other hand, the acceleration sensor 500 having one end open to the outside thereof is similarly designed to prevent the standing wave in the direction along the height L of the closed space V in accordance with the previous conditions.

Figure 13:
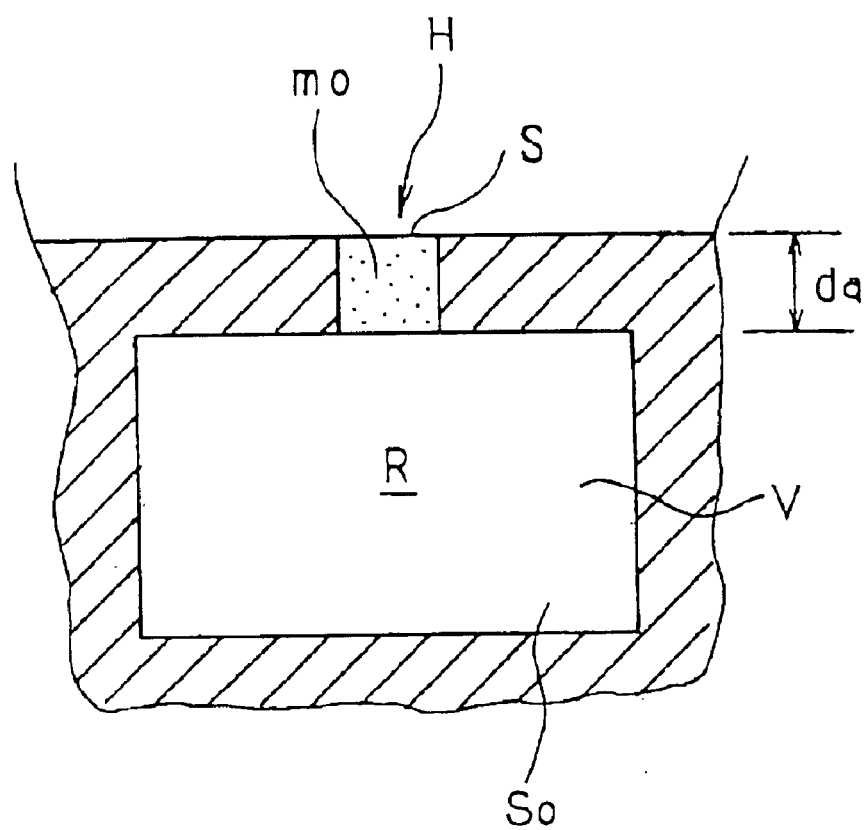
FIG. 13 is a fragmentary cross-sectional view of a model for explaining the generation of the acoustic resonance.

Our review is then directed to an acoustic resonance frequency fh that is detected by a modeled example as shown in FIG. 13. The modeled example is represented by a Helmholtz resonance tube having a chamber R and a nozzle H held in communication with the chamber R and the outside of the resonance tube. The chamber R has a volume v, and the nozzle H has a length da. The resonance tube thus constructed can generate a resonance at its frequency which can be calculated by the following equation. The equation finds that the frequency fh of the acoustic resonance is in proportion to the sonic speed u.

$$fh = (1/2\pi) \times (So/mo)h^{1/2} = (u/2\pi) \times (s/(da \times v))^{1/2}$$

Figure 14:
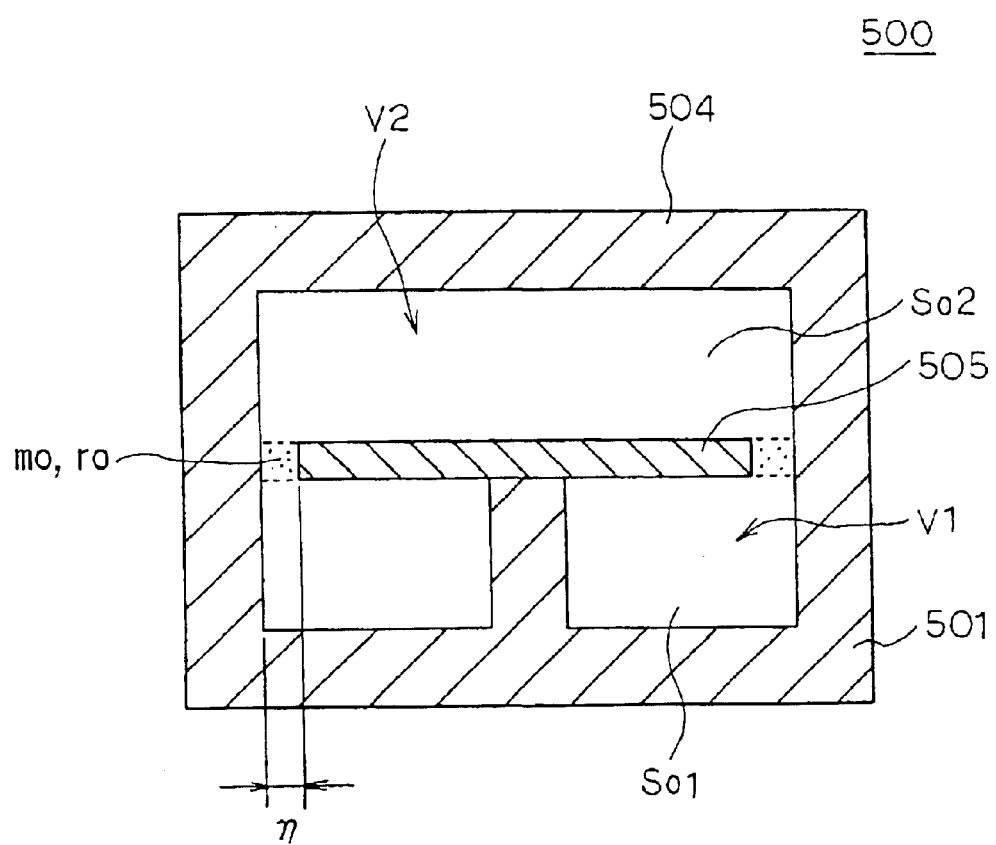
FIG. 14 is a cross-sectional view of a model for explaining the generation of the acoustic resonance.

So: stiffness of air
mo: mass of air
ρ: density of air
$So = \rho \times u^2/v$
$mo = \rho \times da/s$ An attempt has been made to apply the acoustic resonance example to the acceleration sensor 500. FIG. 14 shows a modeled example represented by a roughly drawn acceleration sensor 500 having an annular gap between the inner surface of the fixed case member 501 and the peripheral end of the oscillation body 505. The annular gap has a mass of air mo and a width η. The width η of the annular gap at a relatively small value cannot neglect an acoustic resistance ro. The results of our study confirmed that there is no acoustic resonance generated when the width eta. of the annular gap is below about 0.3 (mm). Here, the closed space sections V1 and V2 formed by the fixed case member 501 and the cover member 504 have respective different stiffness of air values So1 and So2.

Figure 15:
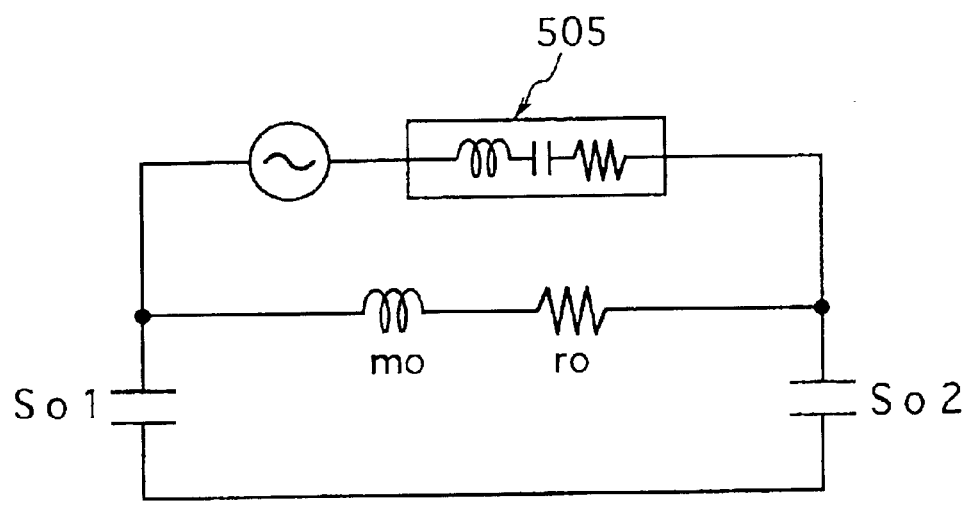
FIG. 15 is a circuit diagram explaining the example of the use of the acceleration sensor according to the present invention.

The acceleration sensor 500 can be modeled into an equivalent circuit shown in FIG. 15. It is confirmed from FIG. 15 that there is an acoustic resonance having a frequency but not two frequencies according to our experimental result. The reason why such a result takes place is considered to be due to the stiffnesses of air So1 and So2 arranged and electrically connected in parallel relationship with each other in the circuit.

The control of the frequency fh of the acoustic resonance by means of the area s of the nozzle H and the length da of the nozzle H in the equation concerning the frequency fh of the acoustic resonance is decided by the diameter of the oscillation body 505 and the inner surface of the fixed case member 501 and the cover member 504. This control can be attained by deciding the desirable resonance frequency fo of the oscillation body 505. The fixed case member 501 and the cover member 504 commonly used make it difficult to control the frequency of the acoustic resonance by means of changing the diameter of the oscillation body 505 while the oscillation body 505 is oscillated at the desirable resonance frequency fo maintained at a constant level.

The control of the frequency fh of the acoustic resonance is eventually easy with the volume v of the chamber R being varied. It is therefore found that the volume v of the chamber R is required to be as small as possible to have the frequency fh of the acoustic resonance raised out of the usable frequency range of the acceleration sensor 500.

The distance L1 between the lower surface of the oscillation body 505 and the upper surface of the bottom portion of the fixed case member 501, and the distance L2 between the upper surface of the oscillation body 505 and the lower surface of the cover member 504 are preferably set at small values for solving the problem on the acoustic resonance in the same way of preventing the standing wave. Through our experimental results, the distances L1 and L2 are to be smaller than about 0.1 times the diameter D of the inner surface of the fixed case member 501 and the cover member 504.

In terms of the acoustic resonance in the acceleration sensor 500, the closed space sections V1 and V2 formed by the fixed case member 501, the cover member 504 and the oscillation body 505 are considered to be in parallel relationship with each other so that the distances L1 and L2 are required to be set at relatively small values but not at lowest values. At least one of the distances L1 and L2 is considered to be set preferably at a small value. Our confirmation indicates that one of the distances L1 and L2 is to be smaller than about 0.05 times the diameter D of the inner surface of the fixed case member 501 and the cover member 504.

In the case of having the acceleration sensor 500 operated at a desirable broad range of frequency with the commonly used the fixed case member 501 and the cover member 504 and with the varied diameter of the oscillation body 505, the closed space sections V1 and V2 formed by the fixed case member 501, the cover member 504 and the oscillation body 505 are to be made narrow so as to prevent the acoustic resonance from being generated in the usable range of the frequency of the acceleration sensor 500 even for the upper limit of the resonance frequency fo of the oscillation body 505.

Figure 16:
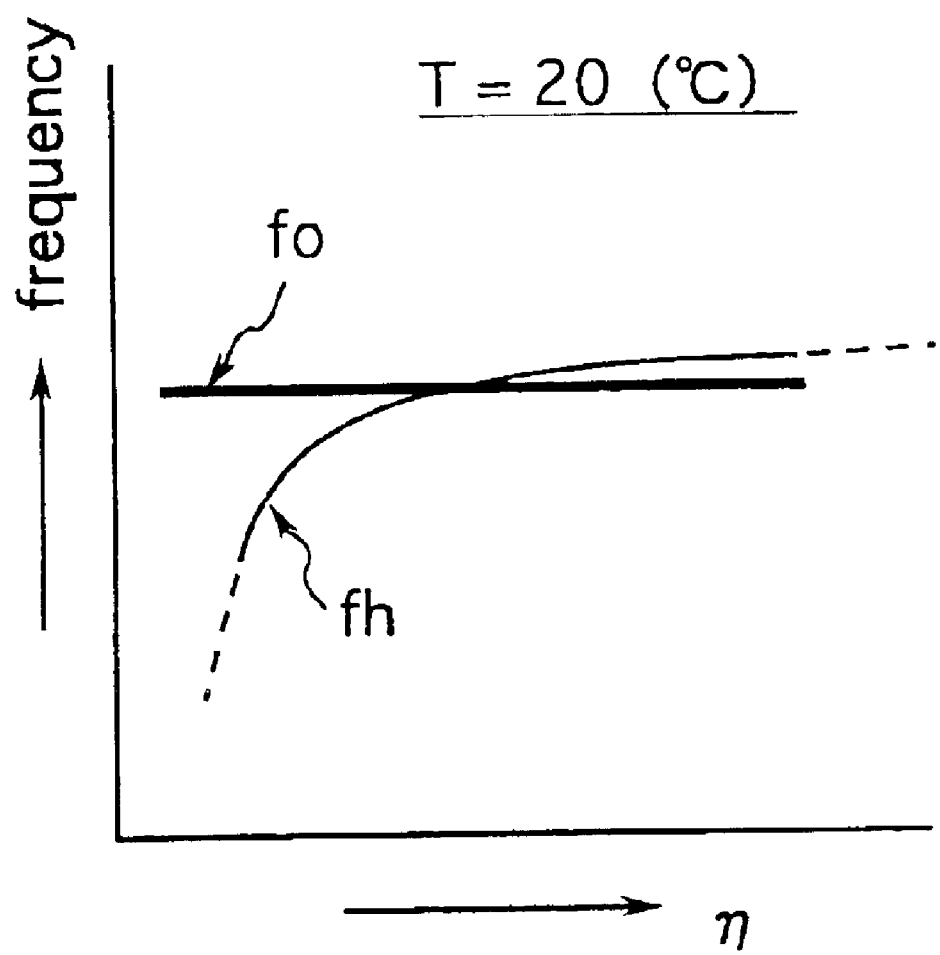
FIG. 16 is a graph showing the experimental results obtained through the experiment of the acceleration sensor according to the present invention.

For example, the closed space sections V1 and V2 relatively small, the varied diameter D of the inner surface of the fixed case member 501 and the cover member 504, and the same diameter of the oscillation body 505 cause the width η of the annular gap to be varied in response to the frequency fh of the acoustic resonance and the constant resonance frequency fo of the oscillation body 505. As will be seen from FIG. 16, the frequency fh of the acoustic resonance is increased to be saturated as the width 91 of the annular gap is increased. The fact that the frequency fh of the acoustic resonance is increased to be saturated as the width η of the annular gap is increased can be understood from the volume v of the chamber R and the area s of the nozzle H both of which is varied in previously mentioned equation representing the frequency fh of the acoustic resonance. From this fact, it will be appreciated that the frequency fh of the acoustic resonance depends on the diameter of the oscillation body 505 when the width η of the annular gap has a certain range of value.

Figure 17:
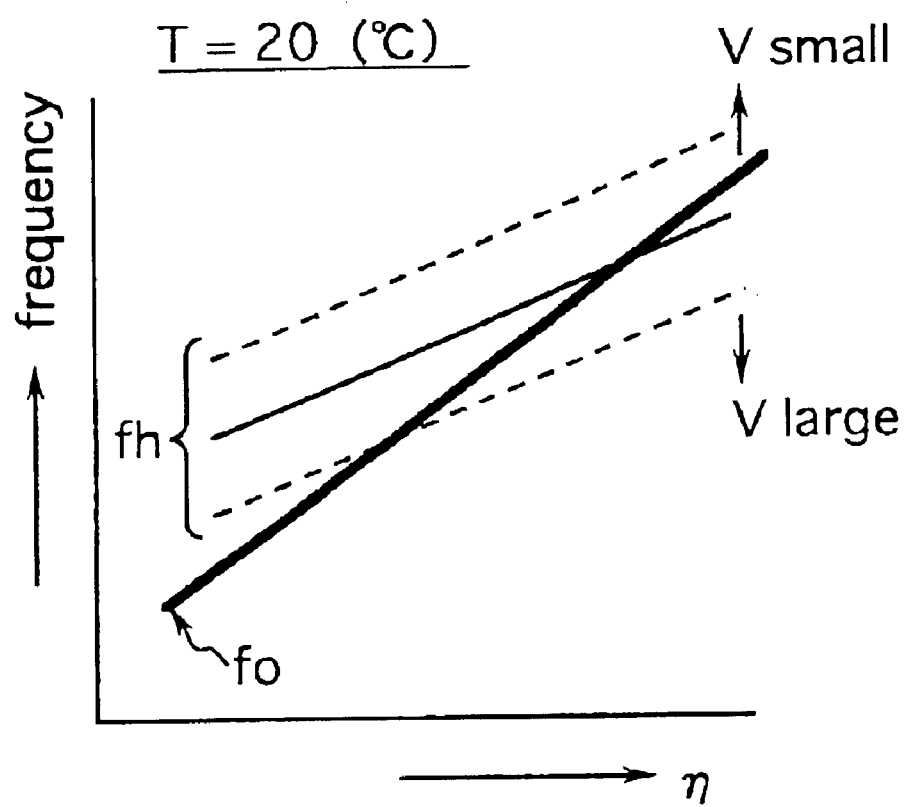
FIG. 17 is a graph showing the experimental results obtained through the experiment of the acceleration sensor according to the present invention.

In the event that the diameter of the oscillation body 505 is varied to have the width η of the annular gap varied the under the condition that the diameter of the fixed case member 501 and the cover member 504 is maintained at a constant value, the following two relations, i.e., the relation between the resonance frequency fo of the oscillation body 505 and the width η of the annular gap, and the frequency fh of the acoustic resonance and the width η of the annular gap are shown in FIG. 17. The resonance frequency fo of the oscillation body 505 and the frequency fh of the acoustic resonance are shown in FIG. 17 as being linearly varied with their respective different inclination angles. The graph shown in FIG. 17 indicates that the small closed space sections V1 and V2 and the frequency fh of the acoustic resonance set at a value higher than that of the resonance frequency fo of the oscillation body 505 bring no effect to the resonance frequency fo of the oscillation body 505.

In the present embodiment of the acceleration sensor 500 thus constructed in the above, the distances L1 and L2 of the closed space sections V1 and V2 are set at respective values less than or equal to 0.1 times the diameter D of the inner surface of the fixed case member 501 and the cover member 504 to ensure that the standing wave is prevented from being generated in the closed space V of the acceleration sensor 500. The closed space sections V1 and V2 small in size can bring the frequency fh of the acoustic resonance out of the upper limit of the usable range of the frequency of the acceleration sensor 500. This means that the acceleration sensor according to the present invention makes it possible to prevent the detection accuracy of the acceleration sensor from deteriorating stemming from the spurious noise caused by the anti-resonance of the standing wave and the acoustic resonance generated in the closed space V, as well as to produce the acceleration sensor at a low cost with the fixed case member and the cover member commonly used and with the oscillation bodies different in diameter.

Figure 18:
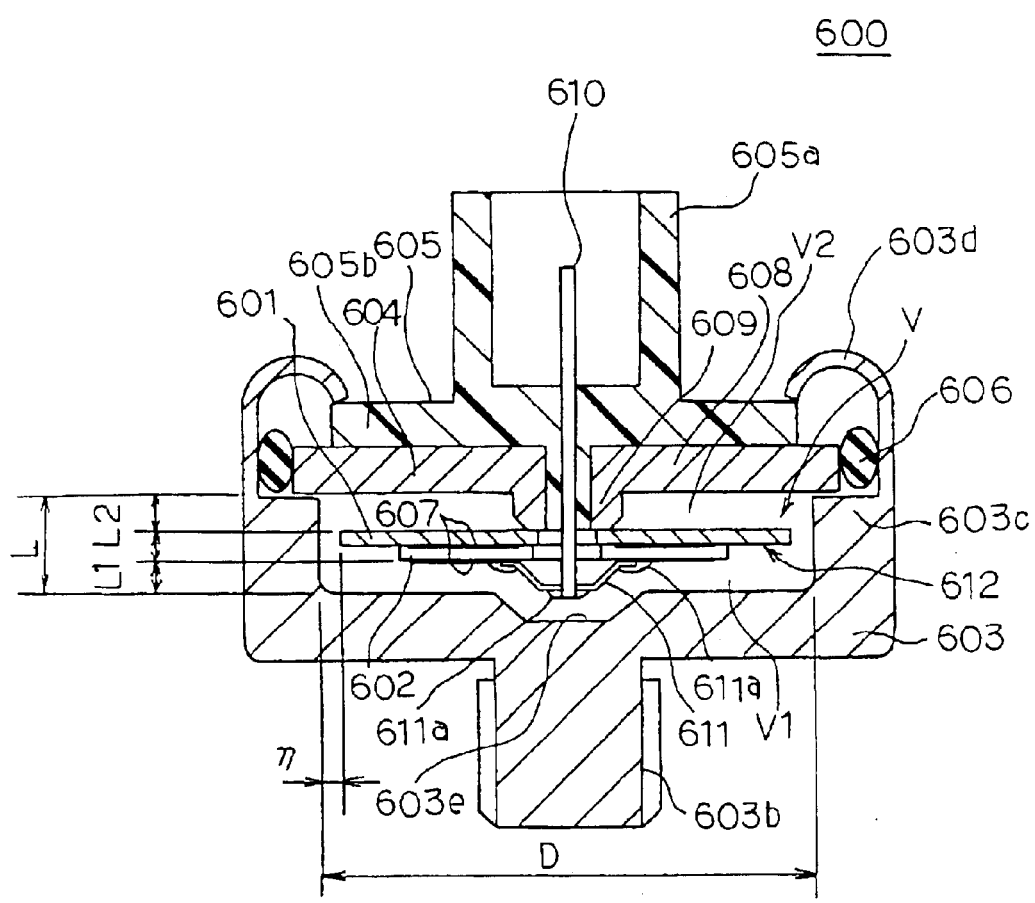
FIG. 18 is a cross-sectional view of the eighth embodiment of the acceleration sensor according to the present invention.

Next, the acceleration sensor exemplified by the eighth embodiment is shown in FIG. 18 to comprise an oscillation plate 601, a piezoelectric element 602, a fixed case member 603, a metal base member 604, a cover member 605, and a resilient ring 606. Similarly to the second conventional acceleration sensor shown in FIG. 27, the piezoelectric element 602 is covered with electrodes 607 and provided on the surface of the oscillation plate 601. This means that the oscillation plate 601 is deformed by being oscillated in response to the acceleration exerted on a detectable object such as an engine. This deformation causes an electrical charge Q to be generated indicative of a voltage V based on the level of a static electricity C of the piezoelectric element 602 so that the acceleration can be detected.

The fixed case member 603 of the eighth embodiment of the acceleration sensor 600 is made of a metal and formed with a cylindrical cavity deeper than that of the seventh embodiment of the acceleration sensor 500. The fixed case member 603 of the eighth embodiment of the acceleration sensor 600 has no supporting portion as formed in the seventh embodiment of the acceleration sensor 500.

The fixed case member 603 has formed on the exterior side thereof a male screw 603*b*, which is to be screwed into a female screw portion formed in a detectable object such as engine. The metal base member 604 formed in a circular shape has a base portion 608 having a second inner surface, and a diameter approximately equal to the fixed case member 603. From the center of the second inner surface of the metal base member 604 is formed to project a supporting portion 609 which is welded to and thus integrally formed with the flat surface of oscillation plate 601 opposite to the piezoelectric element 602. The cover member 605 has a connector portion 605*a* and a disk portion 605*b*. The disk portion 605*b* of the cover member 605 and the central portion of the metal base member 604 have an output terminal pin 610 extend therethrough. The cover member 605 is made of a plastic to ensure that the output terminal pin 610 is electrically insulated from the metal base member 604.

The fixed case member 603 has an annular ledge section 603*c* having the metal base member 604 provided thereon and welded thereto. The fixed case member 603 further has a peripheral edge portion 603*d* radially inwardly bent to be held in contact with the outer peripheral edges of the cover member 605 provided on the metal base member 604. The fixed case member 603 and the cover member 605 collectively define a closed space V to accommodate the oscillation plate 601 and the piezoelectric element 602 to be oscillatable by an oscillation exerted to the acceleration sensor 600. The resilient ring 606 is received in an annular groove between the annular ledge section 603*c* and the inner portion of the peripheral edge portion 603*d* to hermetically seal the gap between the annular ledge section 603*c* and the peripheral edge portion 603*d*. Therefore, no water enters the closed space V through the gap.

The oscillation plate 601 and the piezoelectric element 602 are formed in an annular shape. The output terminal pin 610 extends through the center hole of the oscillation plate 601, the piezoelectric element 602, and the supporting portion 609 of the metal base member 604. The output terminal pin 610 mounted on the cover member 605 is electrically connected to one of the electrodes 607 provided on the piezoelectric element 602. The output terminal pin 610 and one of the electrodes 607 are soldered at 611*a* and thus electrically connected to each other through a resilient metal plate 611 so that the voltage V indicative of an acceleration can be outputted from the piezoelectric element 602.

The resilient metal plate 611 of the acceleration sensor 600 is in the form of a truncated cone shape and projects toward the first inner surface of the fixed case member 603 from the first surface of the piezoelectric element 602. The fixed case member 603 is formed with a central cavity 603*e* in the form of a truncated cone shape and held in opposing relationship with the resilient metal plate 611 when the oscillation body 612 composed of the oscillation plate 601 and the piezoelectric element 602 is accommodated in the closed space V with the distances L1 and L2 in a similar way to the seventh embodiment.

Consequently, the fixed case member 603 and the metal base member 604 collectively defining a closed space V to accommodate therein the oscillation body 612 consisting of the oscillation plate 601 and the piezoelectric element 602 to be oscillated. The fixed case member 603 and the oscillation body 612 define a closed space V1, and the metal base member 604 and the oscillation body 612 define a closed space V2. The distance L1 indicates a distance between the oscillation body 612 and the first inner surface of the fixed case member 603, the distance L2 indicates a distance between the oscillation body 612 and the second inner surface of the metal base member 604. The distance L1 and the distance L2 are respectively set at less than or equal to 0.1 times the diameter D of the inner surface of the fixed case member 603.

The dimension of the acceleration sensor 500 can be also applied to the acceleration sensor 600. The closed space V in the direction along the height L in which the oscillation plate 601 and the piezoelectric element 602 are oscillated can be made narrower than that of conventional acceleration sensor, thereby enabling the acceleration sensor to be made thinner. Therefore, the generation of standing wave in both the direction along the height L of the closed space V and the direction along the diameter D of the inner surface of the fixed case member 11 can be prevented effectively. Further, the fixed case member 603, the metal base member 604, and the cover member 605 can be commonly used as parts or elements of the acceleration sensor 600.

This results in the fact that the eighth embodiment has an advantage and effect the same as that of the seventh embodiment.

While there has been described in the seventh and eighth embodiments an oscillation body having a thickness relatively small, the principle of the present invention may be applied to a oscillation body having a large thickness and a high resonance frequency.

The fact that there is a large difference between the diameters of the oscillation plate and the piezoelectric element leads to the fact that one of the oscillation plate and the piezoelectric element has a surface area exposed to the closed space V larger than that of the other of the oscillation plate and the piezoelectric element. Based on the one of the oscillation plate and the piezoelectric element having a surface area larger than that of the other of the oscillation plate and the piezoelectric element, the space distances L1 and L2 are determined. More specifically, the space distance L1 is measured between the first inner surface of the fixed case member 603 and the surface area of the one of the oscillation plate and the piezoelectric element larger than that of the other of the oscillation plate and the piezoelectric element, while the space distance between the second inner surface of the metal base member 604 and the surface area of the one of the oscillation plate and the piezoelectric larger than that of the other of the oscillation plate and the piezoelectric element. Also, this consideration can be applied in the process of deciding the diameter D1 of the fixed case member 501 and the diameter D2 of the cover member 504.

In the acceleration sensor according to the present invention, the distance L of the closed space V is less than or equal to the diameter of the inner surface of the fixed case member and the cover member multiplied by 0.1, and the space distances L1 and L2 are respectively less than or equal to the diameter of the inner surface of the fixed case member and the cover member multiplied by 0.1. The acceleration sensor thus constructed in the above makes it possible (1) to prevent the detection accuracy of the acceleration sensor from deteriorating stemming from the spurious noise caused by the anti-resonance of the standing wave and the acoustic resonance being generated in the closed space V, and (2) to produce the acceleration sensor at a low cost with the fixed case member and the cover member commonly used.

The effect and advantage of the present invention will be described hereinafter in association with the dimensions of the constitution elements forming the ninth embodiment of the acceleration sensor according to the present invention.

Figure 19:
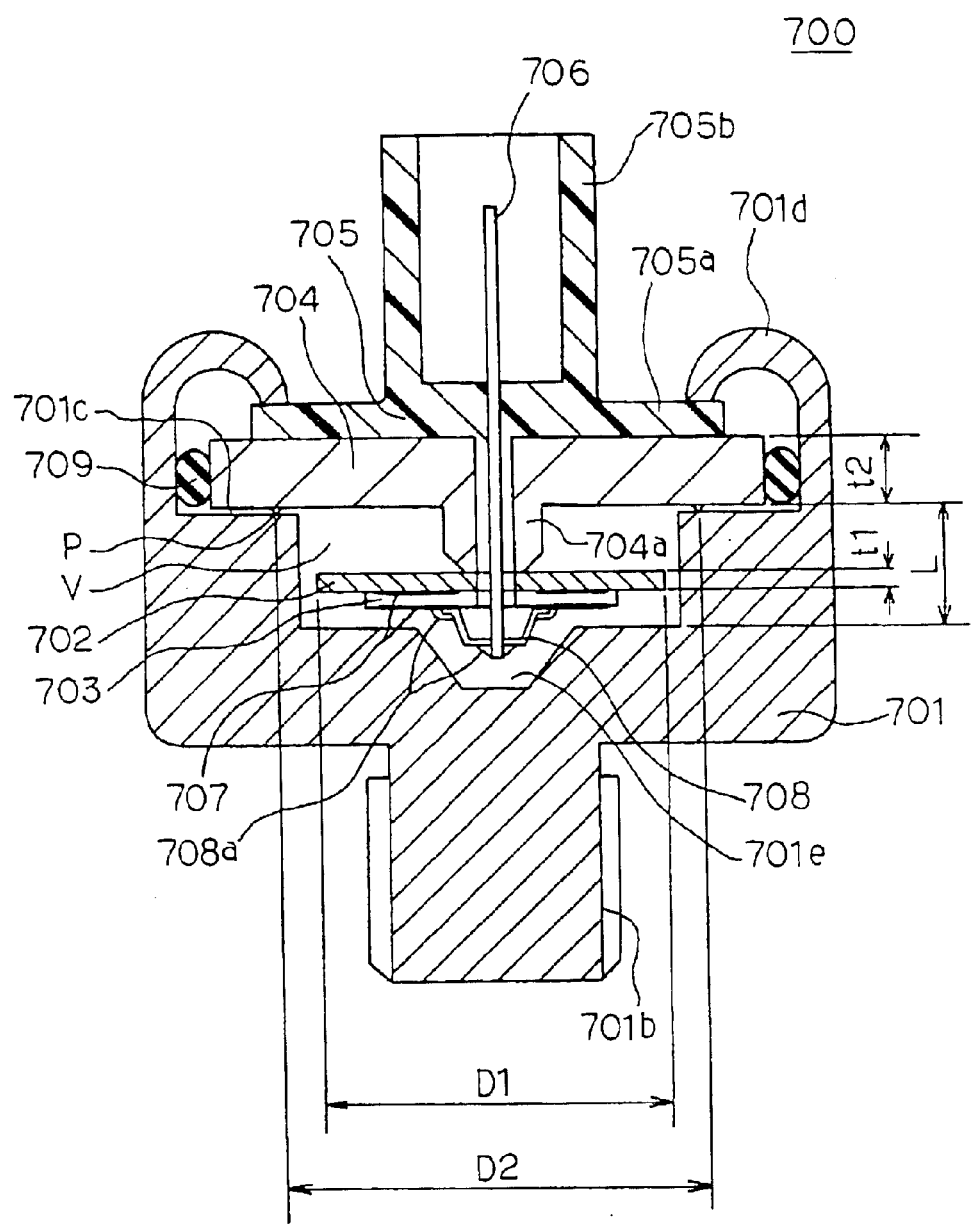
FIG. 19 is a cross-sectional view of the ninth embodiment of the acceleration sensor according to the present invention.

The acceleration sensor exemplified by the ninth embodiment is shown in FIG. 19 to comprise a fixed case member 701, an oscillation plate 702, a piezoelectric element 703, a metal base member 704, a cover member 705, and a resilient ring 709. In a similar fashion to the second conventional acceleration sensor shown in FIG. 27, the oscillation plate 702 made of a metal and in the form of a annular shape has first and second flat surfaces on which are mounted piezoelectric element 703 having thereon electrodes 707, respectively, in coaxial relationship with the oscillation plate 702. This construction of the acceleration sensor 700 makes it possible to generate a certain level of charge Q in response to the stress deformation of the piezoelectric element 703 that is caused by the oscillation of the oscillation plate when the detection object such as for example an automotive engine is subjected to the oscillation. The charge Q of the piezoelectric element 703 has a certain level of capacitance C that is indicative of a certain level of voltage V given by the following equation. In this way, the acceleration sensor 700 can detect a certain level of acceleration.

$$V=Q/C$$

The fixed case member 701 is in the form of a cylindrical shape and has a cylindrical bottom. In this embodiment, the fixed case member 701 has no supporting portion projecting from the cylindrical bottom but has a depth deep enough to accommodate the oscillation plate 702 and the piezoelectric element 703. The fixed case member 701 has a male screw portion 701b formed at its lower portion to be screwed to a female screw portion formed in the detection object such as the engine.

The metal base member 704 has a central portion formed with a supporting portion 704a that is welded to the surface of the oscillation plate 702 opposite to the piezoelectric element 703. The metal base member 704 is substantially equal in diameter to the fixed case member 701. The cover member 705 has a circular portion 705a similar in shape to the metal base member 704, and a connector portion 705b connectable with other exterior objects. The circular portion 705a and the connector portion 705b are made of a plastic and integrally formed with each other.

The cover member 705 has a portion fittedly received in the supporting portion 704a of the metal base member 704 and is designed to receive therein an output terminal pin 706 electrically connected with the exterior objects. The output terminal pin 706 is electrically insulated from the metal base member 704 and has a leading end portion projected out of the oscillation plate 702 and the piezoelectric element 703 to the vicinity of the electrodes 707 of the piezoelectric element 703. Between the electrodes 707 and the leading end portion of the output terminal pin 706 is provided a metal plate 708 that is soldered as at 708a and thus electrically connected with the electrodes 707 and the leading end portion of the output terminal pin 706. It is thus to be understood that the oscillation plate 702 and the piezoelectric element 703 are oscillatably supported by the supporting portion 704a, and that the voltage V generated in the piezoelectric element 703 can be discharged out of the acceleration sensor 700 to the other exterior objects.

The acceleration sensor 700 is constructed to have the metal base member 704 welded to an open end 701c of the fixed case member 701. The cover member 705 is mounted on the metal base member 704. The fixed case member 701 has a peripheral end portion 701d radially inwardly bent and fittedly engaged with the peripheral edge portion of the cover member 705. The fixed case member 701, the metal base member 704 and the cover member 705 constitute as a whole a closed space V adapted to accommodate therein the oscillation plate 702 and the piezoelectric element 703. The fixed case member 701 has a central bottom portion formed with a cavity 701e having therein partly received the metal plate 708 projecting toward the central bottom portion, thereby making it possible to reduce as small as possible the distance between the bottom surface of the fixed case member 701 and the piezoelectric element 703 and the distance between the oscillation plate 702 and the lower surface of the metal base member 704. The resilient ring 709 is located between the peripheral end portion 701d of the fixed case member 701 and the peripheral edge portion of the metal base member 704 to ensure that the closed space V having the oscillation plate 702 and the piezoelectric element 703 accommodated therein is hermetically sealed.

Figure 27:
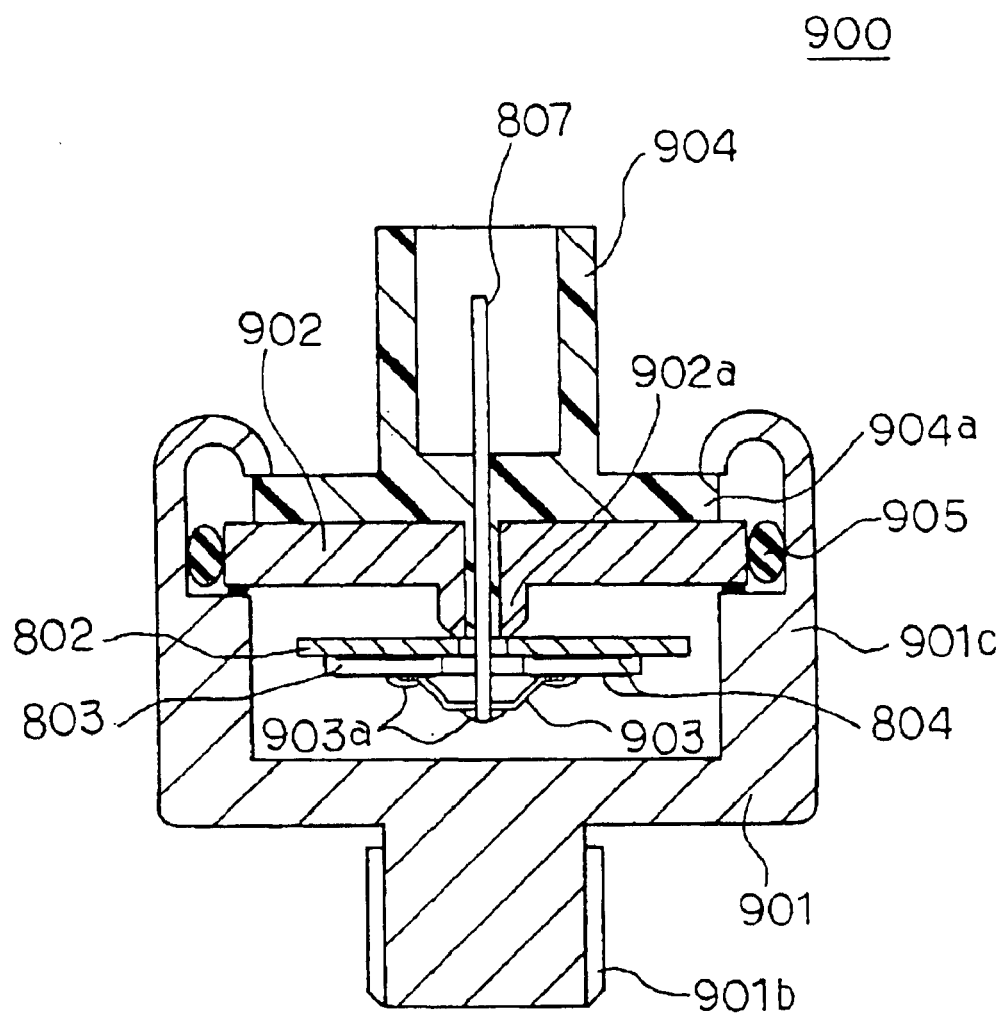
FIG. 27 is a cross-sectional view of the second conventional acceleration sensor.
Figure 28:
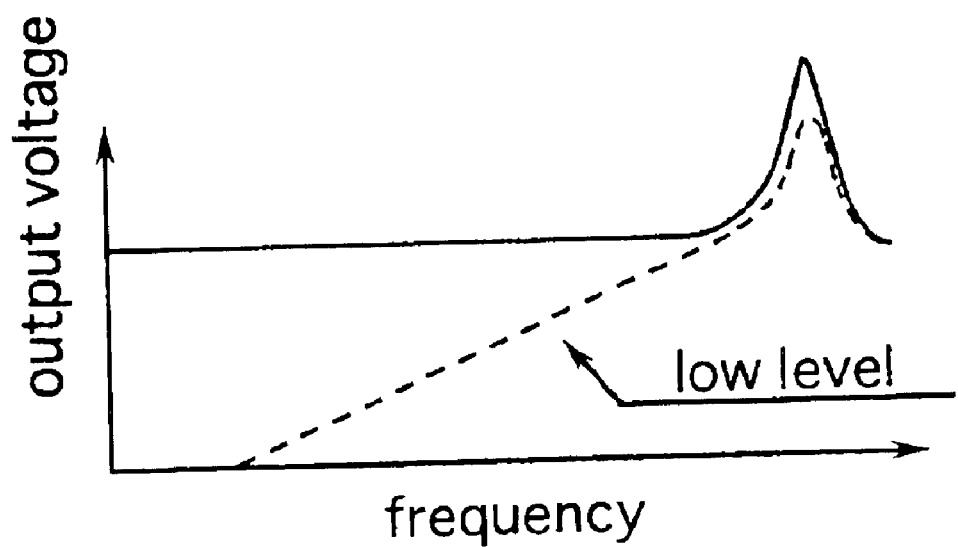
FIG. 28 is a graph showing the resonance characteristic of the first and second conventional acceleration sensors.
Figure 29:
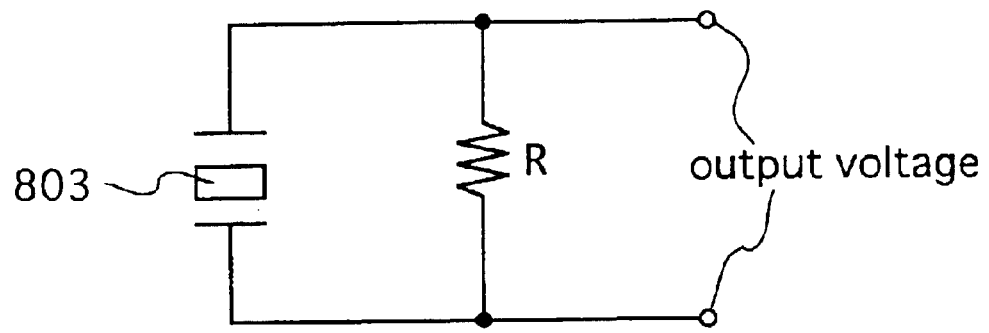
FIG. 29 is a circuit diagram explaining the example of the use of the first and second conventional acceleration sensors.
Figure 30:
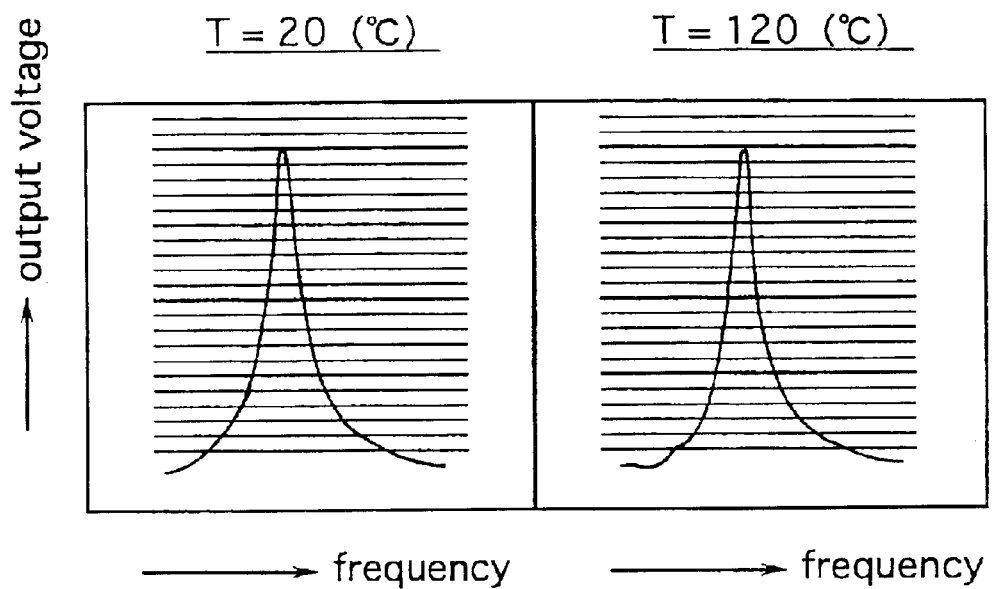
FIG. 30 is a graph showing the resonance characteristic of the first and second conventional acceleration sensors.
Figure 31:
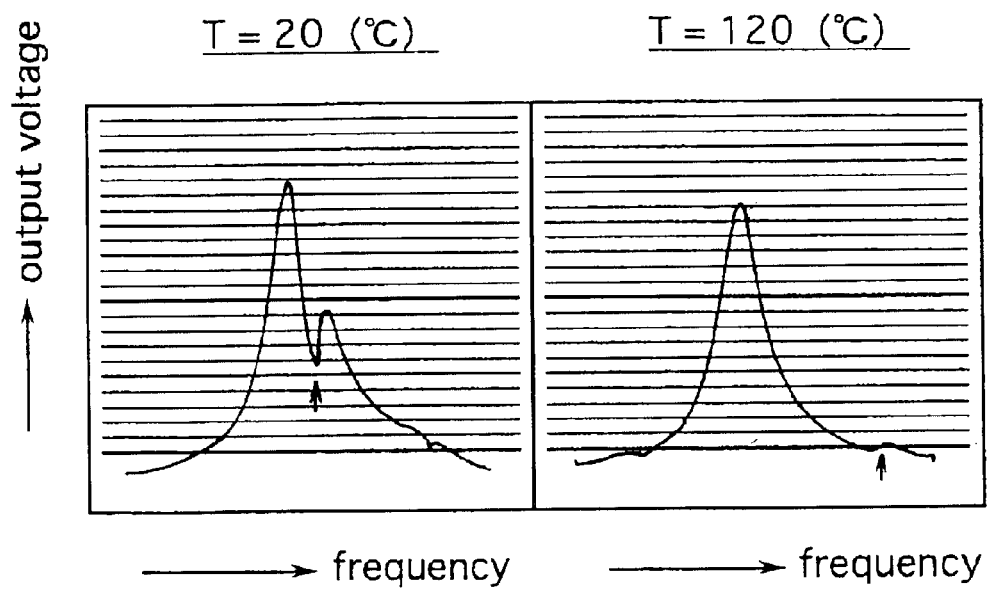
FIG. 31 is a graph showing the resonance characteristic of the first and second conventional acceleration sensors.

The acceleration sensor 700 is constructed to have a structure similar to that of the second conventional acceleration sensor shown in FIG. 27. As will be seen from the foregoing description, the acceleration sensor 700 has the oscillation plate 702 and a piezoelectric element 703 supported by the supporting portion 704a projecting from the metal base member 704 but not supported directly by the bottom portion of the fixed case member 701. This makes it possible to produce an acceleration sensor 700 with a high sensitivity and to realize automatic production thereto.

It will be appreciated that the acceleration sensor 700 can detect the acceleration at a more stable condition and a higher sensitivity than that of the second conventional acceleration sensor if the acceleration sensor 700 is constructed to overcome the drawbacks inherent in the second conventional acceleration sensor. The acceleration sensor 700 is required to be constructed without any noises generated by the phase characteristics of the oscillation transmission other than the oscillation caused by the acceleration but not affected by ambient fluctuated temperatures. For this reason, the acceleration sensor is constructed to have a structure as follows.

(1) The difference between the outer diameter D1 of the oscillation plate 702 and the inner diameter of the fixed case member 701 is set at a minimum level to ensure that the oscillation plate 702 is freely oscillated. The diameter D2 of the welded point P of the metal base member 704 encircling the inner diameter of the fixed case member 701 is set at a value as small as possible. It is most preferable that the diameter D2 of the welded point P of the metal base member 704 be set at a value less than or equal to the outer diameter D1 of the oscillation plate 702 multiplied by 1.4.

(2) The thickness t1 of the oscillation plate 702 is set at a value as small as possible, while the thickness t2 of the metal base member 704 is set at a value as large as possible. It is most preferable that the thickness t2 of the metal base member 704 be set at a value more than or equal to the thickness t1 of the oscillation plate 702 multiplied by about 6.

(3) The height L of the closed space V formed by the fixed case member 701, the metal base member 704 and the cover member 705 is set at a value as small as possible.

(4) The cover member 705 is made of a material having a modulus of elasticity in bending set at a relatively large value and a logarithmic decrement (inner resistance, inner loss) also set at a relatively large value. It is most preferable that the material of the cover member 705 is selected to have a modulus of elasticity in bending set at more than or equal to $8 \times 10^3$ (MPa) and a logarithmic decrement set at more than or equal to 8 (1/s). Our experimental tests confirmed that one of the most preferable materials is a polymer liquid crystal consisting of about 30 percent of glass and about 20 percent of mineral (filler) mixed together. The plastic material of the cover member 705 is required to have high heat resistance that is one of important factors for production of the acceleration sensor.

The previously mentioned items (1), (2) and (3) mean that the resonance frequency fo1 of the fixed case member 701 and the metal base member 704 is more than or equal to about three times the resonance frequency fo of the oscillation plate 702 and the piezoelectric element 703. Further, the previously mentioned items (1) and (3) are concerned with conditions required to prevent the characteristics from deteriorating stemming from the spurious noise caused by the anti-resonance of the acoustic resonance of Helmholtz and the acoustic standing wave being generated in the closed space V, i.e., it is required to set the closed space sections V1 and V2 relatively small in size for the purpose of bringing the frequency of the acoustic resonance out of the upper limit of the usable range of the frequency of the acceleration sensor, and it is required to set a relatively large acoustic resistance in the closed space V for the purpose of preventing the standing wave from being generated in the closed space V. Further, the previously mentioned item (4) is concerned with a condition required to reduce the influence of the oscillation of cover member 705 on the oscillation of the oscillation plate 702 and the piezoelectric element 703. This reduction of the influence is realized by having the cover member 705 composed of solid material to impart the increased resonance frequency to the cover member 705, and by having the cover member 705 composed of the material that has low sharpness of resonance Q and low influence of temperatures change to reduce the amplification of the cover member 705. Here, the sharpness of resonance Q means sensitivity of resonance.

The following description will be directed to the acceleration sensor in term of its dimension design and material selection. The acceleration sensor 700 is produced by welding the fixed case member 701 and the metal base member 704 with the closed space V accommodating therein the oscillation plate 702 and the piezoelectric element 703. These constitution elements and parts of the acceleration sensor 700 have respective following dimensions and characteristics with respect to one example.

<Oscillation Plate 702> outer diameter D1: $\phi 16.9$ (mm)

thickness t1: 0.5 (mm)

modulus of elasticity E: $2 \times 10^{11}$ (N/m$^2$)

density $\rho$: $7.8 \times 10^3$ (kg/m$^3$)

Poisson's ratio $\sigma$: 0.28

<Piezoelectric Element 703> outer diameter: $\phi 12.5$ (mm)

thickness: 0.45 (mm)

modulus of elasticity E: $6.3 \times 10^{10}$ (N/m$^2$)

density $\rho$: $7.65 \times 10^{10}$ (kg/m$^3$)

Poisson's ratio $\rho$: 0.34

Figure 20A:
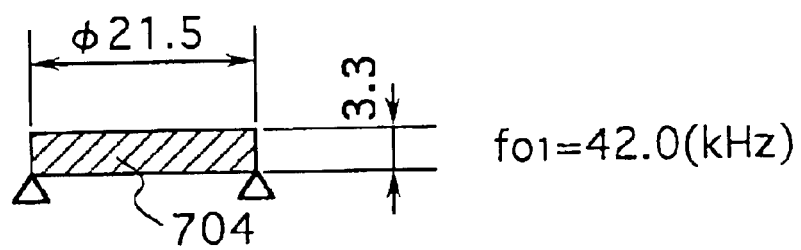
FIG. 20A is a cross-sectional view of model for explaining the dimensions of the constitution elements forming part of the acceleration sensor according to the present invention.
Figure 20B:
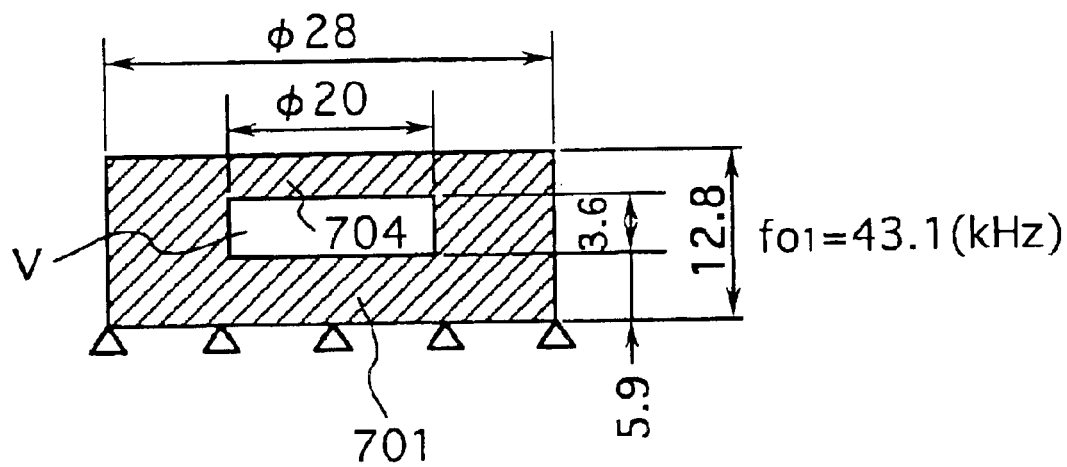
FIG. 20B is a cross-sectional view of model for explaining the dimensions of the constitution elements forming part of the acceleration sensor according to the present invention.

On the other hand, the metal base member 704 is designed to have a dimension as shown in FIG. 20A and welded to the fixed case member 701 with the welded point P having a diameter D2 set at 20 (mm). FIG. 20B illustrates a simplified experimental model of an acceleration sensor in which the dimension of the fixed case member 701 and the metal base member 704 are shown. Temperature characteristic and anti-oscillation characteristic are studied through our repeated experiments as shown in FIG. 20B. The legends appearing with "Δ" in FIG. 20B indicate arresting points at which the fixed case member and the metal base member combined are retained by the exterior object such as an automotive engine. Here, the term "arresting points" is intended to mean fixed points set to see the movement of an experimentally modeled object. Also, the fixed case member 701 and the metal base member 704 are each made of a material the same as the oscillation plate 702 in properties including modulus of elasticity E, density $\rho$ and Poisson's ratio$\sigma$.

Figure 21A:
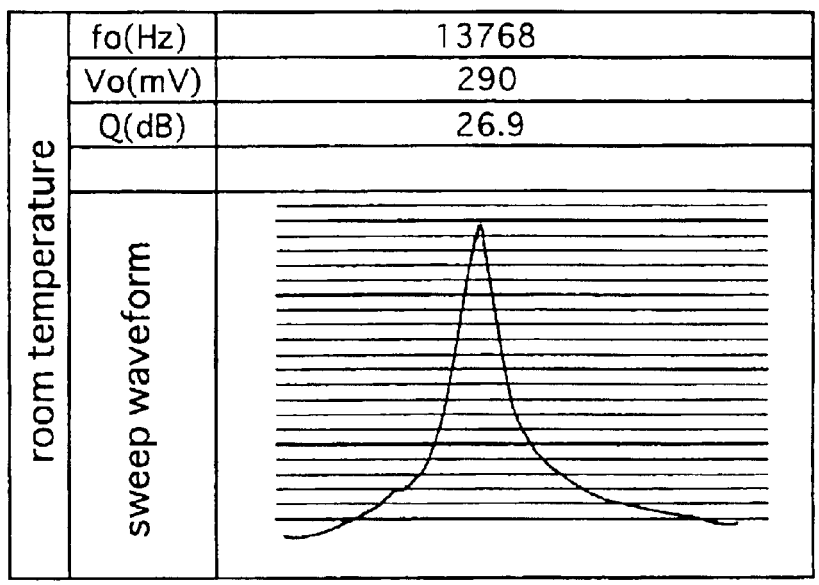
FIG. 21A is a graph showing the experimental results obtained through the experiment of the acceleration sensor according to the present invention.
Figure 21B:
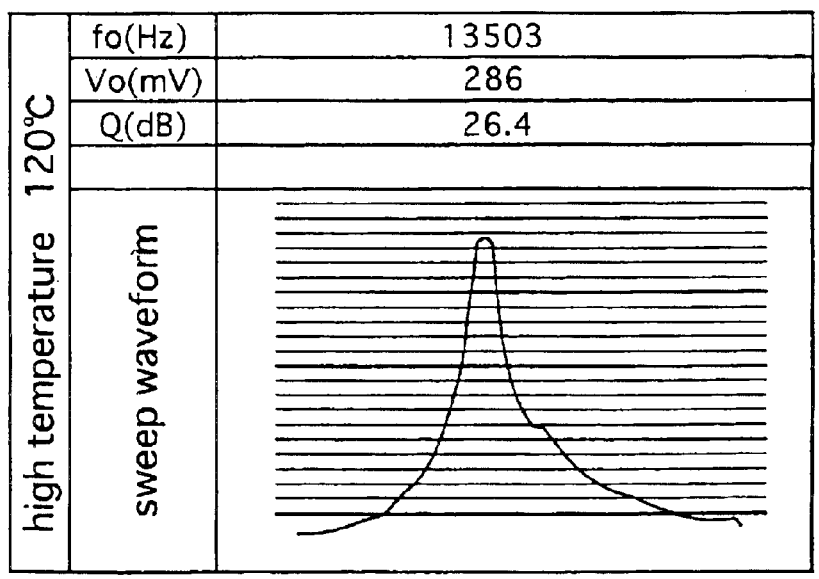
FIG. 21B is a graph showing the experimental results obtained through the experiment of the acceleration sensor according to the present invention.

Under these conditions, the oscillation plate 702 and the piezoelectric element 703 have a resonance frequency fo set at 14 (kHz). It is confirmed that there is no practical problem as seen from FIGS. 21A and 21B with respect to any measurable objects such as high frequency accelerations. Here, judgment is made on whether or not the following range covers several different changed data obtained at high temperatures as compared with the data obtained at room temperatures. If the following range covers those data, there is no practical problem.

Change of the resonance frequency fo: less than or equal to 2%

Change of the sensitivity Vo: less than or equal to 10%

Change of the sharpness of resonance Q (dB): less than or equal to 1 (dB)

Change of the sensitivity caused by oscillation noises: less than or equal to 2 (dB)

The acceleration sensor constructed under the three conditions consisting of a first condition (1) of having the diameter D2 of the welded point P of the metal base member 704 set at less than or equal to 1.4 times the outer diameter D1 of the oscillation plate 702, a second condition (2) of having the thickness t2 of the metal base member 704 set at more than or equal to six times the thickness t1 of the oscillation plate 702, and a third condition (3) of having the height L of the closed space V defined by the fixed case member 701 and the metal base member 704 set at a value as small as possible is considered leading to the fact that the resonance frequency fo1 of the fixed case member 701 and the metal base member 704 is raised sufficiently as compared with the resonance frequency fo of the oscillation plate 702 and the piezoelectric element 703. The above fact is also considered into the fact that the oscillation transmission of the constitution elements of the acceleration sensor is not affected from their oscillation phases, but the sensitivity Vo of the acceleration sensor 700 depends only on the displacement of the oscillation plate 702 and the piezoelectric element 703.

Figure 23A:
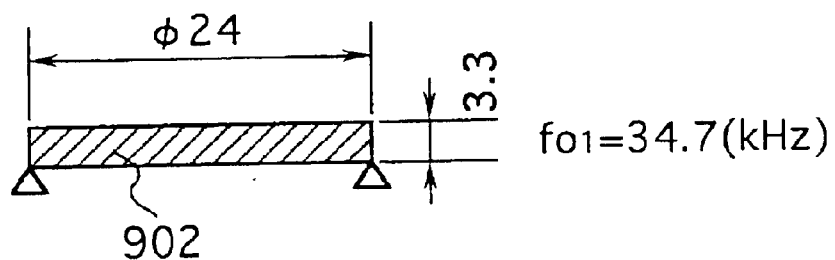
FIG. 23A is a cross-sectional view of model for explaining the dimensions of the constitution elements forming part of the second conventional acceleration sensor.
Figure 23B:
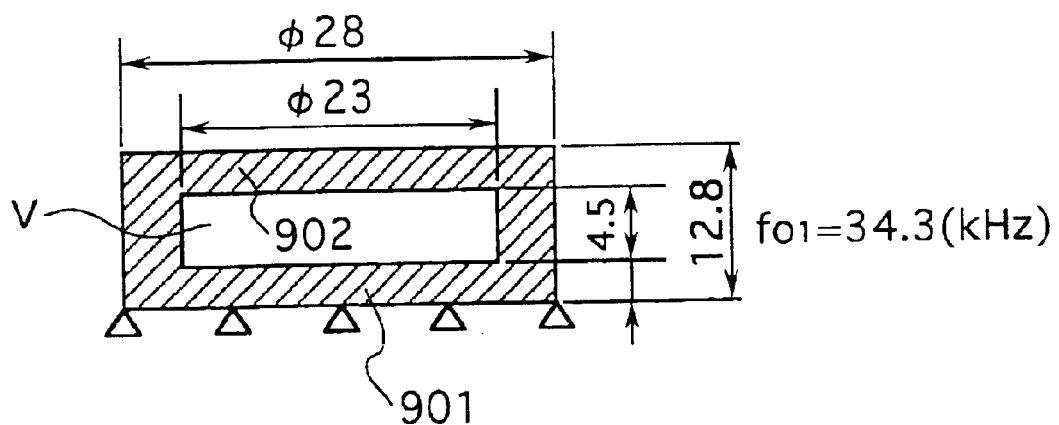
FIG. 23B is a cross-sectional view of model for explaining the dimensions of the constitution elements forming part of the second conventional acceleration sensor.
Figure 24A:
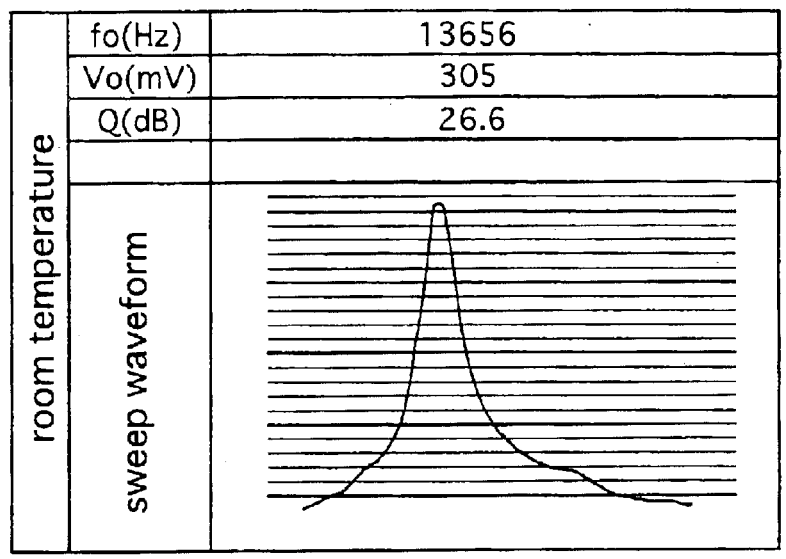
FIG. 24A is a graph showing the experimental results obtained through the experiment of the second conventional acceleration sensor.
Figure 24B:
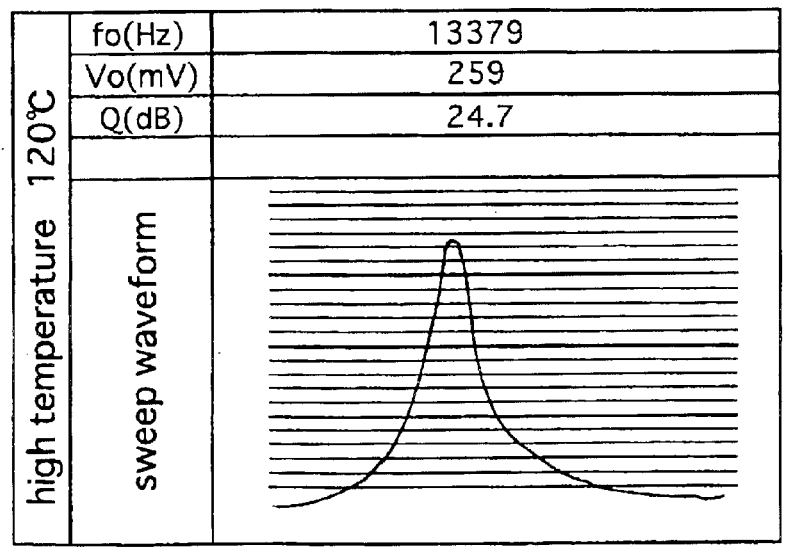
FIG. 24B is a graph showing the experimental results obtained through the experiment of the second conventional acceleration sensor.
Figure 25:
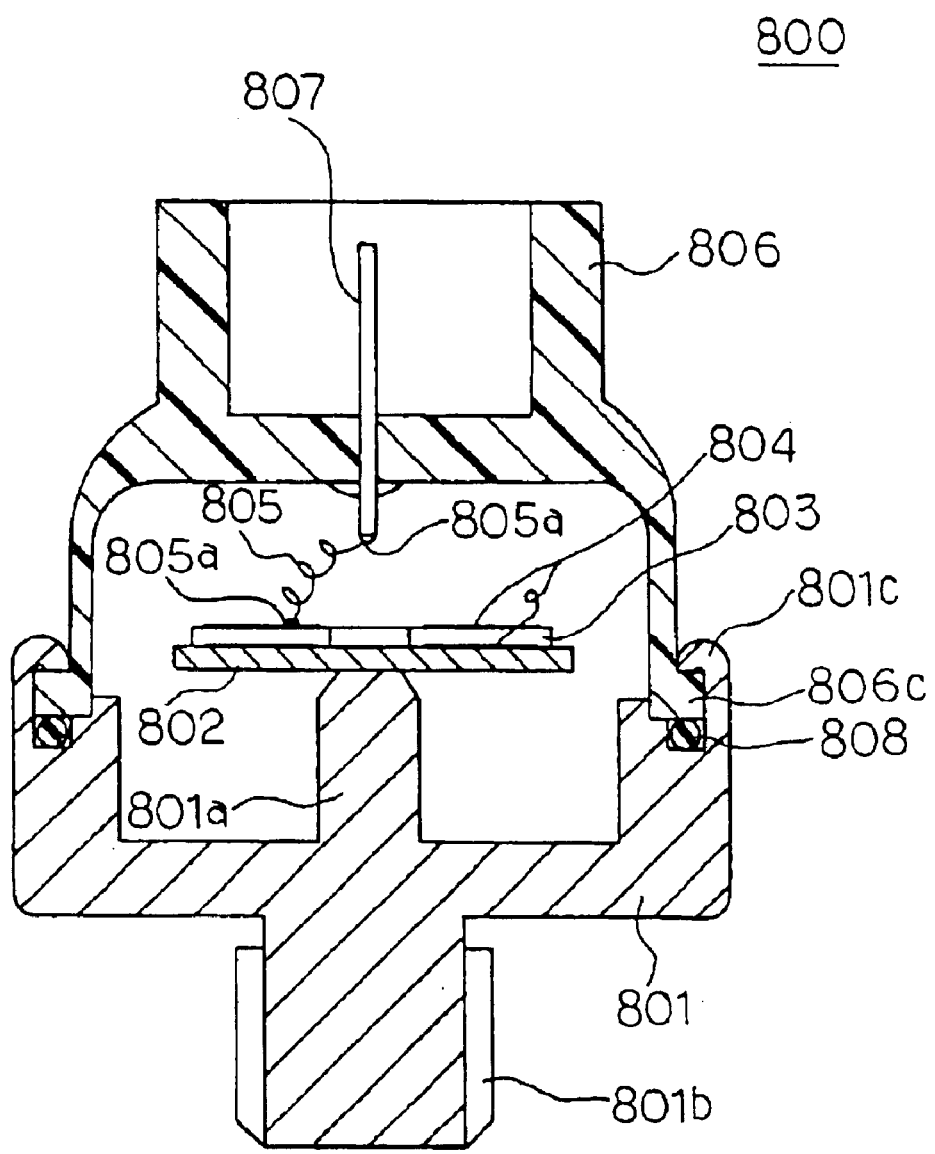
FIG. 25 is a cross-sectional view of the first conventional acceleration sensor.
Figure 26:
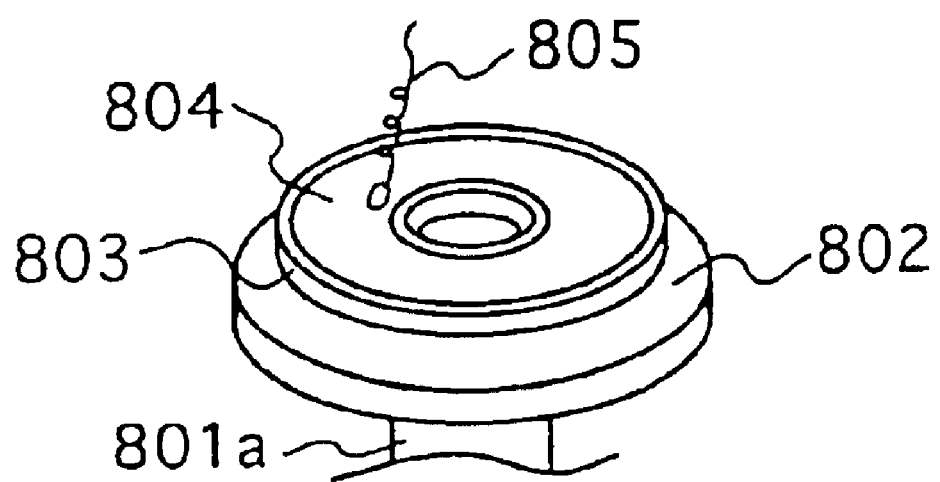
FIG. 26 is a perspective view of the essential elements forming part of the first conventional acceleration sensor.

The second conventional acceleration sensor, on the other hand, is shown in FIG. 27 to have a metal base member 902 that is manufactured with its dimension shown in FIG. 23A to be welded to the fixed case member 901. The experimental model is shown in FIG. 23B as being constituted by the fixed case member 901 and the metal base member 902. The experimental results find that temperature characteristics and anti-oscillation characteristic of the acceleration sensor are deteriorated enough to make it impossible to accurately detect the acceleration of the detection object when the resonance frequency fo of the oscillation plate 702 and the piezoelectric element 703 is at a level beyond about 11 (kHz). If the resonance frequency fo of the oscillation plate 702 and the piezoelectric element 703 is set at 14 (kHz), it is almost impossible to realize a practically usable acceleration sensor as will be seen from FIGS. 24A and 24B.

Through various experimental results, it is found that the resonance frequency fo1 of the fixed case member 701 and the metal base member 704 is preferably more than or equal to three times the resonance frequency fo of the oscillation plate 702 and the piezoelectric element 703 in view of the fact that the acceleration sensor is deteriorated in its characteristic in the range exceeding about 11 (kHz) of the resonance frequency fo of the oscillation plate 702 and the piezoelectric element 703 with respect to about 34 (kHz) of the resonance frequency fo1 of the fixed case member 701 and the metal base member 704 in the second conventional acceleration sensor. More specifically, the resonance frequency fo of the oscillation plate 702 and the piezoelectric element 703 set at about 11 (kHz) is found to require the resonance frequency fo1 of the fixed case member 701 and the metal base member 704 to be set at more than or equal to three times the resonance frequency fo of the oscillation plate 702 and the piezoelectric element 703. In a similar way, the resonance frequency fo of the oscillation plate 702 and the piezoelectric element 703 set at about 14 (kHz) is found from FIGS. 20A and 20B to require the resonance frequency fo1 of the fixed case member 701 and the metal base member 704 to be set at more than or equal to three times the resonance frequency fo of the oscillation plate 702 and the piezoelectric element 703.

If the diameter D2 of the welded point P between the metal base member 704 and the fixed case member 701 is set at a value as small as possible, the metal base member 704 in itself is oscillated at a small amount of displacement, thereby causing enhanced stability and relatively low sensitivity Vo to the acceleration sensor. The experiment confirmed that this example has a sensitivity Vo of about 2 to 3 (dB) higher than that of the first conventional acceleration sensor example in a practical stability. To increase the resonance frequency fo1 of the fixed case member 701 and the metal base member 704, any means other than the dimensions set in the present embodiment can be adopted. The means includes one of measures to select an anti-oscillation characteristic as materials of the fixed case member 701 and the metal base member 704.

The relationship between the diameter D2 of the welded point P of the metal base member 704 and the outer diameter D1 of the oscillation plate 702, as well as the relationship the thickness t2 of the metal base member 704 and the thickness t1 of the oscillation plate 702 will be described hereinafter.

The resonance frequency fo and the sensitivity Vo of the oscillation plate 702 and the piezoelectric element 703 depend on the composed oscillation characteristics of the oscillation plate 702 and the piezoelectric element 703, but are dominated by the constants of the oscillation plate 702 and the piezoelectric element 703. In view of the above fact, the oscillation plate 702 is considered dominant to influence the resonance frequency fo and the sensitivity Vo of the oscillation plate 702 and the piezoelectric element 703. In order to reduce the sharpness of resonance Q of the acceleration sensor 700, the outer diameter of the piezoelectric element 703 is required to be smaller than the outer diameter D1 of the oscillation plate 702. Especially in this case, the resonance frequency fo and the sensitivity Vo is decided mainly in consideration of the oscillation plate 702. This means that it is most effective that the optimum conditions required for designing the acceleration sensor 700 be considered in view of the oscillation plate 702.

The experiment of changing the diameter D2 of the welded point P of the metal base member 704 and the outer diameter D1 of the oscillation plate 702 is conducted under the conditions shown in FIGS. 20A and 20B and set at various dimensions as follows to obtain experimental results shown in FIG. 22.

<Oscillation Plate 702>
outer diameter D1: φ18.4, φ16.9 (mm)
thickness t1: 0.5 (mm)
<Piezoelectric Element 703>
outer diameter: φ12.5 (mm).
thickness: 0.45 (mm)
<Metal Base Member 704>
diameter D2: φ24, φ21.5 (mm)
thickness t2: 3.3 (mm)

Figure 22:
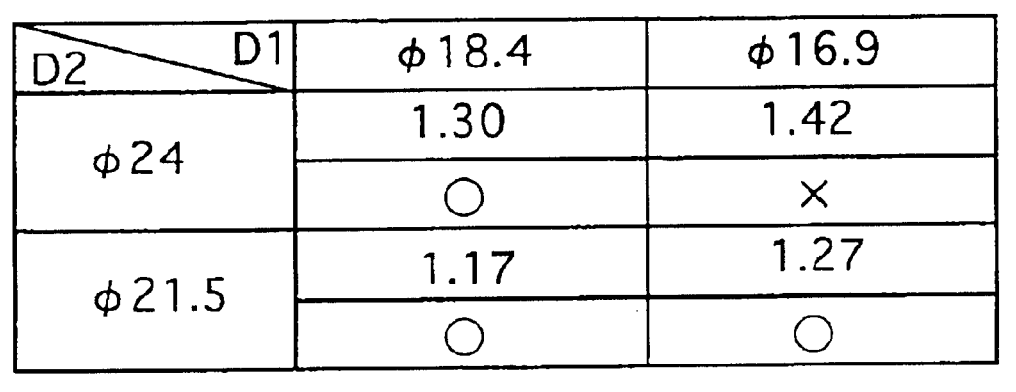

The table shown in FIG. 22 indicates the experimental results on whether the following characteristics are within acceptable ranges or not.

Change of the resonance frequency fo: less than or equal to 2%
Change of the sensitivity Vo: less than or equal to 10%
Change of the sharpness of resonance Q (dB): less than or equal to 1 (dB)
Change of the sensitivity caused by oscillation noises: less than or equal to 2 (dB)

For example, for our first experiment made under the condition that the outer diameter D1 of the oscillation plate 702 is φ16.9 while the diameter D2 of the welded point P of the metal base member 704 is φ24, the above characteristics are not within acceptable ranges as shown by the legend "X" as a result of D2/D1=1.42. As for our second experiment made under the condition that the outer diameter D1 of the oscillation plate 702 is φ18.4 while the diameter D2 of the welded point P of the metal base member 704 is φ24, the above characteristics are within acceptable ranges as shown by the legend "○" due to D2/D1=1.30. Also, for our third experiment made under the condition that the outer diameter D1 of the oscillation plate 702 is φ16.9 while the diameter D2 of the welded point P of the metal base member 704 is φ21.5, the above characteristics are within acceptable ranges as shown by the legend "○" resulting from D2/D1=1.27. Similarly, for our fourth experiment made under the condition that the outer diameter D1 of the oscillation plate 702 is φ18.4 while the diameter D2 of the welded point P of the metal base member 704 is φ21.5, the above characteristics are within acceptable ranges as shown by the legend "○" stemming from D2/D1=1.17.

From the foregoing experimental results, it is to be understood that the diameter D2 of the welded point P of the metal base member 704 is found set preferably at less than or equal to 1.4 times the outer diameter D1 of the oscillation plate 702, and more preferably less than or equal to 1.3 times the outer diameter D1 of the oscillation plate 702. The thickness t2 of the metal base member 704 depends on the diameter D2 of the welded point P of the metal base member 704. Because of the fact that it is most preferable that the thickness t2 of the metal base member 704 be 3.3 (mm) against 0.5 (min) of the thickness t1 of the oscillation plate 702, the thickness t2 of the metal base member 704 is required to be set at more than or equal to six times the thickness t1 of the oscillation plate 702.

As will be appreciated from the foregoing description, the diameter D2 of the welded point P of the metal base member 704 set preferably at less than or equal to 1.4 times the outer diameter D1 of the oscillation plate 702 and the thickness t2 of the metal base member 704 set at more than or equal to six times the thickness t1 of the oscillation plate 702 result in the fact that the displacement of the metal base member 704 cannot influence the displacement of the oscillation plate 702, thereby making it possible to have the acceleration sensor detect the acceleration of the detection object in a stable condition and without any deviation.

The various experimental results find that the cover member 705 is made of a plastic material preferably selected to have a modulus of elasticity in bending set at more than or equal to $8\times10^3$ (MPa) and a logarithmic decrement set at more than or equal to 8 (1/s). The selection of the material is extremely important for the improved and stabilized temperature characteristics and the strengthened exterior oscillation noises to the acceleration sensor 700. The cover member 705 is most preferably made of a polymer liquid crystal that is advantageous in terms of heat and oscillation resistances as compared with PBT (polybutyrene terephthalate) contained with anti-oscillation material usually on market and nylon. It is confirmed that most preferable material is a polymer liquid crystal containing for example about 30% of glass and about 20% of mineral (filler).

In this embodiment of the present invention, the property of the plastic material is represented by a modulus of elasticity in bending and a logarithmic decrement. Both of the modulus of elasticity in bending and the logarithmic decrement effectively contribute the advantage of the acceleration sensor, however, are acceptable even if both values of the modulus of elasticity in bending and a logarithmic decrement are deviated to some extent in the allowable range set forth in the foregoing description.

As a consequence, the acceleration sensor according to the present invention can have a cover member improved in anti-heat and raised in resonance frequency. The cover member can be made large in internal resistance and loss and thus has a small amount of the sharpness of resonance Q. Moreover, the cover member can be reduced in oscillation and enhanced in stability to the ambient temperatures as well as can lower noise level caused by the external oscillations of the output terminal pin.

In the present embodiment, the oscillation plate 702 and the piezoelectric element 703 are not directly supported by the fixed case member 701 securely mounted on the detection object such as engines and the like, but by the metal base member 704 having a peripheral edge portion welded to the peripheral edge of the fixed case member 701 to define a closed space V accommodating therein the oscillation plate 702 and the piezoelectric element 703. The acceleration sensor thus constructed in the above makes it possible to automatically produce and assemble the acceleration sensor of relatively high sensitivity at a low cost.

The acceleration sensor is constructed to have the fixed case member 701, the oscillation plate 702, and the metal base member 704 set at their respective optimum values to make the resonance frequency fo1 of the overall sensor casing, including the fixed case member 701, the metal base member 704 and the cover member 705, more than or equal to three times the resonance frequency fo of the oscillation plate 702 and the piezoelectric element 703, and to have the cover member 705 made of a material preferably selected to have a modulus of elasticity in bending set at more than or equal to a predetermined value and a logarithmic decrement set at more than or equal to a predetermined value. The acceleration sensor thus constructed in the above enables its temperature characteristics to be stabilized and can avoid the influence caused by the oscillation noises.

In the acceleration sensor according to the present invention, the oscillation plate and the piezoelectric element are not directly supported by the fixed case member, but by the metal base member. The cover member is made of a material preferably selected to have a modulus of elasticity in bending and a logarithmic decrement both of which is set at more than or equal to respective predetermined values, and the resonance frequency of the fixed case member and the metal base member is set at more than or equal to three times the resonance frequency of the oscillation plate and the piezoelectric element. The acceleration sensor thus constructed in the above makes it possible (1) to automatically produce and assemble the acceleration sensor of relatively high sensitivity, (2) to stabilize the temperature characteristics of the acceleration, (3) to avoid the influence of the oscillation noises, (4) to produce the acceleration sensor at a low cost, and (5) to produce the acceleration sensor of relatively high performance.

What is claimed is:

1. An acceleration sensor for detecting an acceleration caused by an object oscillated in an oscillation direction, comprising:

a sensor casing having a center axis and to be positioned in coaxial alignment with said oscillation direction to receive said acceleration, said sensor casing including a cylindrical fixed case member having a circular bottom portion having a first circular inner surface, and a cylindrical side portion integrally formed with said bottom portion, said side portion of said fixed case member having a first section close to said bottom portion of said fixed case member, a second section remote from said bottom portion of said fixed case member and radially inwardly bent, and an annular ledge section formed between said first and second sections with an annular ledge, a metal base member having a circular base portion and a supporting portion, said base portion having a second circular inner surface and a circular outer surface, and said supporting portion projecting from said second inner surface, said base portion of said metal base member having a central section integrally formed with said supporting portion, and a peripheral section extending radially outwardly of said central section, said metal base member mounted on said annular ledge of said fixed case member with a resilient ring intervening between said second section of said side portion of said fixed case member and said peripheral section of said base portion of said metal base member to hermetically seal the gap between said second section of said side portion of said fixed case member and said peripheral section of said base portion of said metal base member, said first section of said side portion of said fixed case member having a third cylindrical inner surface connected at one end with said first inner surface of said bottom portion of said fixed case member and at the other end with said second inner surface of said base portion of said metal base member, said second inner surface of said base portion of said metal base member opposing to and spaced apart along said center axis from said first inner surface of said bottom portion of said fixed case member at a first space distance, and a cover member being provided on said outer surface of said metal base member and having a peripheral section firmly engaged with said second section of said side portion of said fixed case member, said first inner surface of said bottom portion of said fixed case member, said second inner surface of said base portion of said metal base member, and said third inner surface of said first section of said side portion of said fixed case member collectively defining a cylindrical closed space;

an oscillation plate accommodated in said closed space of said sensor casing and having a central portion securely supported by said supporting portion of said metal base member of said sensor casing, and a peripheral portion integrally formed with said central portion and extending radially outwardly of said central portion to be freely movable with respect to said sensor casing, said oscillation plate having a peripheral end surface spaced apart from said third inner surface of said first section of said side portion of said fixed case member at an annular gap small enough to enable said oscillation plate to oscillate with respect to said sensor casing, said oscillation plate having a first flat surface opposing to and spaced apart along said center axis from said first inner surface of said bottom portion of said fixed case member at a second space distance, and a second flat surface opposing to and spaced apart along said center axis from said second inner surface of said base portion of said metal base member at a third space distance, said oscillation plate being partly oscillatable along said center axis with respect to said sensor casing; and a piezoelectric element having first and second surfaces and provided on at least one of said first and second flat surfaces of said oscillation plate in axial alignment with said oscillation plate to generate a voltage indicative of said acceleration when said acceleration is exerted on said sensor casing to have said oscillation plate partly oscillated along said center axis with respect to said sensor casing with said peripheral portion of said oscillation plate being deformed, said oscillation plate and said piezoelectric element collectively constituting an oscillation body; in which the resonance frequency of said sensor casing is more than or equal to the resonance frequency of said oscillation body multiplied by 3, and in which the modulus of elasticity in bending of said cover member is more than or equal to $8 \times 10^3$ (MPa), and the logarithmic decrement of said cover member is more than or equal to 8 (1/s).

2. An acceleration sensor as set forth in claim 1, in which said fixed case member and said metal base member are made of a metal, and said cover member is made of a polymer liquid crystal.

3. An acceleration sensor as set forth in claim 1, said metal base member having a circumferential section firmly connected to said annular ledge section of said side portion of said fixed case member, in which the diameter of said circumferential section of said metal base member is less than or equal to the diameter of said oscillation plate multiplied by 1.4, and the thickness of said metal base member is more than or equal to the thickness of said oscillation plate multiplied by 6.

4. An acceleration sensor as set forth in claim 1, in which said piezoelectric element is in the form of an annular shape and provided on said first flat surface of said oscillation plate, and said piezoelectric element has said first surface opposing to said first inner surface of said bottom portion of said fixed case member and having thereon a first electrode opposing to said first inner surface of said bottom portion of said fixed case member, and said second surface held in contact with said first flat surface of said oscillation plate and having thereon a second electrode between said second surface of said piezoelectric element and said first flat surface of said oscillation plate, in which said first and second electrodes enable said voltage indicative of said acceleration to output therethrough.

5. An acceleration sensor as set forth in claim 1, in which said piezoelectric element is in the form of an annular shape and provided on said second flat surface of said oscillation plate, and said piezoelectric element has said first surface held in contact with said second flat surface of said oscillation plate and having thereon a first electrode between said first surface of said piezoelectric element and said second flat surface of said oscillation plate, and said second surface opposing to said second inner surface of said base portion of said metal base member and having thereon a second electrode opposing to said second inner surface of said base portion of said metal base member, in which said first and second electrodes enable said voltage indicative of said acceleration to output therethrough.

6. An acceleration sensor as set forth in claim 1, which further comprises an output terminal pin mounted on said cover member and partly extending through said cover member, said supporting portion of said metal base member, said oscillation plate, and said piezoelectric element into said closed space to be electrically connected to said piezoelectric element, in which said output terminal pin has a terminal end portion projecting outwardly of said cover member and electrically connectable with an exterior coupling member to output said voltage indicative of said acceleration.

7. An acceleration sensor as set forth in claim 1, in which said fixed case member has a screw portion to be screwed to said object which is to receive said acceleration.

8. An acceleration sensor as set forth in claim 1, in which said supporting portion of said metal base member projects toward said bottom portion of said fixed case member and is tapered toward said oscillation plate and formed with a through bore.

9. An acceleration sensor as set forth in claim 1, which further comprises a resilient metal plate in the form of a truncated cone shape and having an open end electrically connectable with said piezoelectric element.

10. An acceleration sensor as set forth in claim 9, in which said bottom portion of said fixed case member is formed with a central cavity plate open toward said metal plate and in the form similar to said shape of said metal plate.

11. An acceleration sensor as set forth in claim 1, in which said oscillation plate has a central hole formed at the center portion thereof and open at said first and second flat surfaces, in which said piezoelectric element has a central hole formed at the center portion thereof and open at its first and second surfaces.

12. An acceleration sensor for detecting an acceleration caused by an object oscillated in an oscillation direction, comprising:

a sensor casing having a center axis and to be positioned in coaxial alignment with said oscillation direction to receive said acceleration, said sensor casing including a cylindrical fixed case member having a circular bottom portion having a first circular inner surface, and a cylindrical side portion integrally formed with said bottom portion, said side portion of said fixed case member having a first section close to said bottom portion of said fixed case member, a second section remote from said bottom portion of said fixed case member and radially inwardly bent, and an annular ledge section formed between said first and second sections with an annular ledge, a metal base member having a circular base portion and a supporting portion, said base portion having a second circular inner surface and a circular outer surface, and said supporting portion projecting from said second inner surface, said base portion of said metal base member having a central section integrally formed with said supporting portion, and a peripheral section extending radially outwardly of said central section, said metal base member mounted on said annular ledge of said fixed case member with a resilient ring intervening between said second section of said side portion of said fixed case member and said peripheral section of said base portion of said metal base member to hermetically seal the gap between said second section of said side portion of said fixed case member and said peripheral section of said base portion of said metal base member, said first section of said side portion of said fixed case member having a third cylindrical inner surface connected at one end with said first inner surface of said bottom portion of said fixed case member and at the other end with said second inner surface of said base portion of said metal base member, said second inner surface of said base portion of said metal base member opposing to and spaced apart along said center axis from said first inner surface of said bottom portion of said fixed case member at a first space distance, and a cover member being provided on said outer surface of said metal base member and having a peripheral section firmly engaged with said second section of said side portion of said fixed case member, said first inner surface of said bottom portion of said fixed case member, said second inner surface of said base portion of said metal base member, and said third inner surface of said first section of said side portion of said fixed case member collectively defining a cylindrical closed space;

an oscillation plate accommodated in said closed space of said sensor casing and having a central portion securely supported by said supporting portion of said metal base member of said sensor casing, and a peripheral portion integrally formed with said central portion and extending radially outwardly of said central portion to be freely movable with respect to said sensor casing, said oscillation plate having a peripheral end surface spaced apart from said third inner surface of said first section of said side portion of said fixed case member at an annular gap small enough to enable said oscillation plate to oscillate with respect to said sensor casing, said oscillation plate having a first flat surface opposing to and spaced apart along said center axis from said first inner surface of said bottom portion of said fixed case member at a second space distance, and a second flat surface opposing to and spaced apart along said center axis from said second inner surface of said base portion of said metal base member at a third space distance, said oscillation plate being partly oscillatable along said center axis with respect to said sensor casing;

a first piezoelectric element having first and second surfaces and provided on said first flat surface of said oscillation plate in axial alignment with said oscillation plate to generate a voltage indicative of said acceleration when said acceleration is exerted on said sensor casing to have said oscillation plate partly oscillated along said center axis with respect to said sensor casing with said peripheral portion of said oscillation plate being deformed; and a second piezoelectric element having first and second surfaces and provided on said second flat surface of said oscillation plate in axial alignment with said oscillation plate to generate a voltage indicative of said acceleration when said acceleration is exerted on said sensor casing to have said oscillation plate partly oscillated along said center axis with respect to said sensor casing with said peripheral portion of said oscillation plate being deformed, said oscillation plate and said first and second piezoelectric elements collectively constituting an oscillation body; in which the resonance frequency of said sensor casing is more than or equal to the resonance frequency of said oscillation body multiplied by 3, and in which the modulus of elasticity in bending of said cover member is more than or equal to $8 \times 10^3$ (MPa), and the logarithmic decrement of said cover member is more than or equal to 8 (1/s).

13. An acceleration sensor as set forth in claim 12, in which said fixed case member and said metal base member are made of a metal, and said cover member is made of a polymer liquid crystal.

14. An acceleration sensor as set forth in claim 12, said metal base member having a circumferential section firmly connected to said annular ledge section of said side portion of said fixed case member, in which the diameter of said circumferential section of said metal base member is less than or equal to the diameter of said oscillation plate multiplied by 1.4, and the thickness of said metal base member is more than or equal to the thickness of said oscillation plate multiplied by 6.

15. An acceleration sensor as set forth in claim 12, in which said first piezoelectric element is in the form of an annular shape and provided on said first flat surface of said oscillation plate, and said first piezoelectric element has said first surface opposing to said first inner surface of said bottom portion of said fixed case member and having thereon a first electrode opposing to said first inner surface of said bottom portion of said fixed case member, and said second surface held in contact with said first flat surface of said oscillation plate and having thereon a second electrode between said second surface of said first piezoelectric element and said first flat surface of said oscillation plate, in which said first and second electrodes of said first piezoelectric element enable said voltage indicative of said acceleration to output therethrough, in which said second piezoelectric element is in the form of an annular shape and provided on said second flat surface of said oscillation plate, and said second piezoelectric element has said first surface held in contact with said second flat surface of said oscillation plate and having thereon a first electrode between said first surface of said second piezoelectric element and said second flat surface of said oscillation plate, and said second surface opposing to said second inner surface of said base portion of said metal base member and having thereon a second electrode opposing to said second inner surface of said base portion of said metal base member, in which said first and second electrodes of said second piezoelectric element enable said voltage indicative of said acceleration to output therethrough.

16. An acceleration sensor as set forth in claim 12, which further comprises an output terminal pin mounted on said cover member and partly extending through said cover member, said supporting portion of said metal base member, said oscillation plate, and said piezoelectric element into said closed space to be electrically connected to said piezoelectric element, in which said output terminal pin has a terminal end portion projecting outwardly of said cover member and electrically connectable with an exterior coupling member to output said voltage indicative of said acceleration.

17. An acceleration sensor as set forth in claim 12, in which said fixed case member has a screw portion to be screwed to said object which is to receive said acceleration.

18. An acceleration sensor as set forth in claim 12, in which said supporting portion of said metal base member projects toward said bottom portion of said fixed case member and is tapered toward said oscillation plate and formed with a through bore.

19. An acceleration sensor as set forth in claim 12, which further comprises a resilient metal plate in the form of a truncated cone shape and having an open end electrically connectable with said first piezoelectric element.

20. An acceleration sensor as set forth in claim 19, in which said bottom portion of said fixed case member is formed with a central cavity plate open toward said metal plate and in the form similar to said shape of said metal plate.

21. An acceleration sensor as set forth in claim 12, in which said oscillation plate has a central hole formed at the center portion thereof and open at said first and second flat surfaces, in which said first piezoelectric element has a central hole formed at the center portion thereof and open at its first and-second surfaces, in which said second piezoelectric element has a central hole formed at the center portion thereof and open at its first and second surfaces.

* * * * *